(12) United States Patent  (10) Patent No.: US 7,186,814 B2
Garimella et al.  (45) Date of Patent: Mar. 6, 2007

(54) BIOCONJUGATE-NANOPARTICLE PROBES

(75) Inventors: Viswanadham Garimella, Evanston, IL (US); James J. Storhoff, Evanston, IL (US)

(73) Assignee: Nanosphere, Inc., Northbrook, IL (US)

( * ) Notice: Subject to any disclaimer, the term of this patent is extended or adjusted under 35 U.S.C. 154(b) by 579 days.

(21) Appl. No.: 10/291,291

(22) Filed: Nov. 8, 2002

(65) Prior Publication Data

US 2003/0143598 A1 Jul. 31, 2003

Related U.S. Application Data

(60) Provisional application No. 60/348,239, filed on Nov. 9, 2001.

(51) Int. Cl.
C07H 21/00 (2006.01)
C07H 21/02 (2006.01)
C07H 21/04 (2006.01)
C12Q 1/68 (2006.01)

(52) U.S. Cl. .................. 536/23.1; 536/24.3; 536/25.3; 435/6

(58) Field of Classification Search ................ 536/23.1, 536/24.3, 25.3; 435/6
See application file for complete search history.

(56) References Cited

U.S. PATENT DOCUMENTS

| 4,193,983 A | 3/1980 | Ullman et al. |
| 4,256,834 A | 3/1981 | Zuk et al. |
| 4,261,968 A | 4/1981 | Ullman et al. |
| 4,313,734 A | 2/1982 | Leuvering |
| 4,318,707 A | 3/1982 | Litman et al. |
| 4,650,770 A | 3/1987 | Liu et al. |
| 4,713,348 A | 12/1987 | Ullman |
| 4,853,335 A | 8/1989 | Olsen et al. |
| 4,868,104 A | 9/1989 | Kurn et al. |
| 4,996,143 A | 2/1991 | Heller et al. ................... 435/6 |
| 5,225,064 A | 7/1993 | Henkens et al. |
| 5,284,748 A | 2/1994 | Mroczkowski et al. |
| 5,288,609 A | 2/1994 | Engelhardt et al. |
| 5,294,369 A | 3/1994 | Shigekawa et al. |
| 5,360,895 A | 11/1994 | Hainfeld et al. |
| 5,384,073 A | 1/1995 | Shigekawa et al. |
| 5,384,265 A | 1/1995 | Kidwell et al. |
| 5,460,831 A | 10/1995 | Kossovsky et al. |
| 5,472,881 A | 12/1995 | Beebe et al. |
| 5,514,602 A | 5/1996 | Brooks, Jr. et al. |
| 5,521,289 A * | 5/1996 | Hainfeld et al. ......... 530/391.5 |
| 5,543,158 A | 8/1996 | Gref et al. |
| 5,571,726 A | 11/1996 | Brooks, Jr. et al. |
| 5,599,668 A | 2/1997 | Stimpson et al. |
| 5,609,907 A | 3/1997 | Natan |
| 5,637,508 A | 6/1997 | Kidwell et al. |
| 5,665,582 A | 9/1997 | Kausch et al. |
| 5,681,943 A | 10/1997 | Letsinger et al. |
| 5,751,018 A | 5/1998 | Alivisatos et al. |
| 5,830,986 A | 11/1998 | Merrill et al. ............... 528/332 |
| 5,900,481 A | 5/1999 | Lough et al. ............... 536/55.3 |
| 5,939,021 A | 8/1999 | Hansen et al. |
| 5,990,479 A | 11/1999 | Weiss et al. |
| 6,025,202 A | 2/2000 | Natan |
| 6,149,868 A | 11/2000 | Natan et al. |
| 6,203,989 B1 | 3/2001 | Goldberg et al. ............... 435/6 |
| 6,214,560 B1 | 4/2001 | Yguerabide et al. .......... 435/7.1 |
| 6,251,303 B1 | 6/2001 | Bawendi et al. ...... 252/301.4 R |
| 6,277,489 B1 | 8/2001 | Abbott et al. ............... 428/403 |
| 6,306,610 B1 | 10/2001 | Bawendi et al. ............. 435/7.1 |
| 6,361,944 B1 | 3/2002 | Mirkin et al. ................... 435/6 |
| 6,365,418 B1 | 4/2002 | Wagner et al. ............... 436/518 |
| 6,369,206 B1 * | 4/2002 | Leone et al. ............. 530/391.5 |
| 6,417,340 B1 | 7/2002 | Mirkin et al. ............... 536/23.1 |
| 6,720,147 B2 * | 4/2004 | Mirkin et al. ................... 435/6 |
| 2002/0172953 A1 | 11/2002 | Mirkin et al. |
| 2003/0068622 A1 | 4/2003 | Mirkin et al. ................... 435/6 |
| 2003/0068638 A1 | 4/2003 | Mirkin et al. ................... 435/6 |
| 2004/0101889 A1 | 5/2004 | Mirkin et al. ................... 435/6 |

FOREIGN PATENT DOCUMENTS

| EP | 0 630 974 A2 | 6/1994 |
| EP | 0 667 398 A2 | 8/1995 |
| WO | WO 89/06801 | 7/1989 |
| WO | WO 90/02205 | 3/1990 |
| WO | WO 92/04469 | 3/1992 |
| WO | WO 93/10564 | 5/1993 |
| WO | WO 93/25709 | 12/1993 |
| WO | WO 94/29484 | 12/1994 |
| WO | WO 97/40181 | 10/1997 |

(Continued)

OTHER PUBLICATIONS

Letsinger, R., et al., "Chemistry of Oligonucleotide-Gold Nanoparticle Conjugates," *Phosphorus, Sulfur and Silicon*, vol. 144, p. 359-362 (1999).

Letsinger, R., et al., "Use of a Steroid Cyclic Disulfide Anchor in Constructing Gold Nanoparticle—Oligonucleotide Conjugates," *Bioconjugate Chem*, p. 289-291 (2000).

Li Z., et al., "Multiple thiol-anchor capped DNA-gold nanoparticle conjugates," *Nucleic Acids Research*, vol. 30, p. 1558-1562 (2002).

Nuzzo R., et al., "Spontaneously Organized Molecular Assemblies. 3. Preparation and Properties of Solution Adsorbed Monolayers of Organic Disulfides on Gold Surfaces," *J. Am. Chem. Soc.*, vol. 109, p. 2358-2368 (1987).

(Continued)

*Primary Examiner*—Jezia Riley
(74) *Attorney, Agent, or Firm*—McDonnell Boehnen Hulbert & Berghoff, LLP

(57) ABSTRACT

The invention provides nanoparticle-bioconjugate probes that are useful for detecting target analytes such as nucleic acids. The probes of the invention are stable towards heat and resistant to displacement by thiol containing compounds such as DTT (dithiothreitol).

25 Claims, 9 Drawing Sheets

FOREIGN PATENT DOCUMENTS

| WO | WO 98/04740 | 2/1998 |
|---|---|---|
| WO | WO 98/04740 A1 | 2/1998 |
| WO | WO 98/10289 | 3/1998 |
| WO | WO 98/17317 | 4/1998 |
| WO | WO 99/23258 | 10/1998 |
| WO | WO 99/20789 | 4/1999 |
| WO | WO 99/21934 | 5/1999 |
| WO | WO 99/23258 | 5/1999 |
| WO | WO 99/60169 | 11/1999 |
| WO | WO 00/25136 | 5/2000 |
| WO | WO 01/00876 | 1/2001 |
| WO | WO 01/51665 | 7/2001 |
| WO | WO 01/73123 | 10/2001 |
| WO | WO 01/86301 | 11/2001 |
| WO | WO 02/04681 | 1/2002 |
| WO | WO 02/18643 | 3/2002 |
| WO | WO 02/36169 | 5/2002 |
| WO | WO 00/33079 | 6/2002 |
| WO | WO 02/46472 | 6/2002 |
| WO | WO 02/46483 | 6/2002 |
| WO | WO 2004/053105 A2 | 6/2004 |

OTHER PUBLICATIONS

Otsuka, H., et al., "Quantitative and Reversible Lectin-Induced Association of Gold Nonoparticles Modified with α-Lactosyl-ω-mercapto-poly(ethyleneglycol)," *J. Am. Chem. Soc.*, vol. 123, p. 8226-8230 (2001).
Wuelfing, P., et al., "Nanometer Gold Clusters Protected by Surface-Bound Monolayers of Thiolated Poly(ethylene glycol) Polymer Electrolyte," *J. Am. Chem. Soc.*, vol. 120, p. 12696-12697 (1998).
Alivisatos et al., "Organization of 'nanocrystal molecules' using DNA," *Nature*, vol. 382, pp. 609-611 (1996).
Bain, et al., "Modeling Organic Surfaces with Self-Assembled Monolayers," *Angew. Chem. Int. Ed. Engl.*, vol. 28, pp. 506-512 (1989).
Bradley, "The Chemistry of Transition Metal Colloids," *Clusters and Colloids: From Theory to Applications*, G. Schmid, Editor, BCH, Weinheim, New York, pp. 459-542 (1994).
Brust et al., "Novel Gold-Dithiol Nano-Networks with Non-Metallic Electronic Properties," *Adv. Mater.*, vol. 7, pp. 795-797 (1995).
Chen et al., "A Specific Quadrilateral Synthesized from DNA Branched Junctions," *J. Am. Chem. Soc.*, vol. 111, pp. 6402-6407 (1989).
Chen & Seeman, "Synthesis from DNA of a molecule with the connectivity of a cube," *Nature*, vol. 350, pp. 631-633 (1991).
Chen et al., Crystal Structure of a Four-Stranded Intercalated DNA: $d(C_4)^{†‡}$ *Biochem.*, vol. 33, pp. 13540-13546 (1994).
Dagani, "Supramolecular Assemblies DNA to organize gold nanoparticles," *Chemical & Engineering News*, p. 6-7, Aug. 19, 1996.
Dubois & Nuzzo, "Synthesis, Structure, and Properties of Model Organic Surfaces," *Annu. Rev. Phys. Chem.*, vol. 43, pp. 437-464 (1992).
Elghanian et al., "Selective Colorimetric Detection of Polynucleotides Based on the Distance-Dependent Optical Properties of Gold Nanoparticles," *Science*, vol. 277, pp. 1078-1081 (1997).
Grabar et al., "Preparation and Characterization of Au Colloid Monolayers," *Anal. Chem.* vol. 67, pp. 735-743 (1995).
Hacia et al., "Detection of heterozygous mutations in BRCA1 using high density oligonucleotide arrays and two-colour fluorescence analysis," *Nature Genet.*, vol. 14, pp. 441-447 (1996).
Jacoby, "Nanoparticles change color on binding to nucleotide target," *Chemical &Engineering News*, p. 10, Aug. 25, 1997.
Letsinger et al., Use of Hydrophobic Substituents in Controlling Self-Assembly of Oligonucleotides, *J. Am. Chem. Soc.*, vol. 115, pp. 7535-7536 (1993).
Letsinger et al., "Control of Excimer Emission and Photochemistry of Stilbene Units by Oligonucleotide Hybridization," *J. Am. Chem. Soc.*, vol. 116, pp. 811-812 (1994).

Marsh et al., "A new DNA nanostructure, the G-wire, imaged by scanning probe microscopy," *Nucleic Acids Res.*, vol. 23, pp. 696-700 (1995).
Mirkin, "H-DNA and Related Structures," *Annu. Review Biophys. Biomol. Struct.*, vol. 23, pp. 541-576 (1994).
Mirkin et al., "A DNA-based method for rationally assembling nanoparticles into macroscopic materials," *Nature*, vol. 382, pp. 607-609 (1996).
Mirkin et al., "DNA-Induced Assembly of Gold Nanoparticles: A Method for Rationally Organizing Colloidal Particles into Ordered Macroscopic Materials," *Abstract* 249, Abstracts of Papers Part 1, 212 ACS National Meeting 0-8412-3402-7, American Chemical Society, Orlando, FL, Aug. 25-29, 1996.
Mucic et al., "Synthesis and characterizations of DNA with ferrocenyl groups attached to their 5'-termini: electrochemical characterization of a redox-active nucleotide monolayer," *Chem. Commun.*, pp. 555-557 (1996).
Mulvaney, "Surface Plasmon Spectroscopy of Nanosized Metal Particles," *Langmuir*, vol. 12, pp. 788-800 (1996).
Rabke-Clemmer et al., "Analysis of Functionalized DNA Adsorption on Au(111) Using Electron Spectroscopy," *Langmuir*, vol. 10, pp. 1796-1800 (1994).
Roubi, "Molecular Machines—Nanodevice with rotating arms assembled from synthetic DNA," *Chemical & Engineering News*, p. 13, (Jan. 1999).
Seeman et al., "Synthetic DNA knots and catenanes," *New J Chem.*, vol. 17, pp. 739-755 (1993).
Shaw & Wang, "Knotting of a DNA Chain During Ring Closure," *Science*, vol. 260, pp. 533-536 (1993).
Shekhtman et al., "Sterostructure of replicative DNA catenanes from eukaryotic cells," *New J. Chem.* vol. 17, pp. 757-763 (1993).
Smith and Feigon, "Quadruplex structure of Oxytricha telomeric DNA oligonucleotides," *Nature*, vol. 356, pp. 164-168 (1992).
Thein et al., "The use of synthetic oligonucleotides as specific hybridization probes in the diagnosis of genetic disorders," 2nd Ed., K.E. Davies, Ed., Oxford University Press, Oxford, New York, Tokyo, p. 21-33 (1993).
Wang et al., "Assembly and Characterization of Five-Arm and Six-Arm DNA Brached Junctions," *Biochem.*, vol. 30, pp. 5667-5674 (1991).
Wang et al., "A DNA Aptamer Which Binds to and Inhibits Thrombin Exhibits a New Structural Motif for DNA," *Biochem.*, vol. 32, pp. 1899-1904 (1993).
Weisbecker et al., "Molecular Self-Assembly of Aliphatic Thiols on Gold Colloids," *Langmuir*, vol. 12, pp. 3763-3772 (1996).
Wells, "Unusual DNA Structures," *J. Biol. Chem.*, vol. 263, pp. 1095-1098 (1988).
Zhang et al., "Informational Liposomes: Complexes Derived from Cholesteryl-conjugated Oligonucleotides and Liposomes," *Tetrahedron Lett.*, vol. 37, pp. 6243-6246 (1996).
Borman, *Chem.Eng. News*, Dec. 9, 1996, pp. 42-43 (1996).
Tomlinson et al., *Anal. Biochem*, vol. 171, pp. 217-222 (1998).
Brada, et al., "Golden Blot"—Detection of Polyclonal and Monoclonal Antibodies Bound to Antigens on Nitrocellulose by Protein A-Gold Complexes, *Analytical Biochemistry*, vol. 42, pp. 79-83 (1984) U.S.
Dunn, et al., A Novel Method to Map Transcripts: Evidence for homology between an Adenovirus mRNA and Discrete Multiple Regions of the Viral Genome, *Cell*, vol. 12, pp. 23-36, (1997) U.S.
Hacker, High performance Nanogold—Silver in situ hybridisation, *Eur. J. Histochem*, vol. 42, pp. 111-120 (1998) U.S.
Ranki, et al., "Sandwich hybridization as a convenient method for the detection of nucleic acids in crude samples," *Gene*, vol. 21, pp. 77-85 (1983) U.S.
Romano, et al., "An antiglobulin reagent labelled with colloidal gold for use in electron microscopy," *Immunochemistry*, vol. 11, pp. 521-522 (1974) Great Britain.
Stimpson, et al., "Real-time detection of DNA hybridization and melting on oligonucleotide arrays by using optical wave guides," *Proc. Natl. Acad. Sci..*, vol. 92, pp. 6379-6383, California Institute of Technology (1995) U.S.

Storhoff, et al., "Strategies for Organizing Nanoparticles into Aggregate Structures and Functional Materials," *Journal of Cluster Science*, vol. 8, No. 2, pp. 179-217, Plenum Publishing Corporation (1997) U.S.

Storhoff, et al., "One-Pot Colorimetric Differentiation of Polynucleotides with Single Base Imperfections Using Gold Nanparticle Probes," *J. Am. Chem. Soc.*, vol. 20, pp. 1961-1964, American Chemical Society (1998) U.S.

Velev, et al., "In Situ Assembly of Colloidal Particles into Miniaturized Biosensors," *Langmuir*, vol. 15, No. 11, pp. 3693-3698, American Chemical Society (1999) U.S.

Zhu, et al., "The First Raman Spectrum of an Organic Monolayer on a High-Temperature Superconductor: Direct Spectroscopic Evidence for a Chemical Interaction between an Amine and $Yba_2Cu_3O_{7-\delta}$," *J. Am. Chem. Soc.*, vol. 119, pp. 235-236, American Chemical Society (1997) U.S.

Yguerabide, et al., "Light-Scattering Submicroscopic Particles as Highly Fluorescent Analogs and Their Use as Tracer Labels in Clinical and Biological Applications," I. Theory, *Analytical Biochemistry*, vol. 262, pp. 137-156 (1998) U.S.

Yguerabide, et al., "Light-Scattering Submicroscopic Particles as Highly Fluorescent Analogs and Their Use as Tracer Labels in Clinical and Biological Applications," II. Experimental Characterization, *Analytical Biochemistry*, vol. 262, pp. 157-176 (1998) U.S.

Caruthers et al., "Chemical Synthesis of Deoxyoligonucleotides by the Phosphoramidite Method," *Methods in Enzymology*, vol. 154, p. 287-313 (1987).

Letsinger et al., "Tailored Hydrophbic Cavitites of Oligonucleotide-Steroid Conjugates," *Bioconjugate Chem.*, vol. 9, p. 826-830 (1998).

Pierce, 2-Iminothiolane.HC1 (Traut's Reagent), No. 26101, p. 1-3. TechNote #205 Rev. #002, Section V. Coupling Protocols, Heading A. Carboxyl-Modified Microspheres, pp. 4 and 5 (Aug. 31, 1999).

Zammatteo, et al., "Comparison between Different Strategies of Covalent Attachment of DNA to Glass Surfaces to Build DNA Microarrays," Analytical Biochem., vol. 280, 143-150 (2000).

Mohanty J., et al. "Pulsed laser excitation of phosphate stabilized silver nanoparticles," *Proc. Indian Acd. Sci.*, vol. 112, No. 1, p. 63-72.

Nicewarmer- Peña S., et al., "Hybridization and Enzymatic Extension of Au Nanoparticle-Bound Oligonucleotides," *J. Am. Chem. Soc.*, vol. 124, p. 7314-7323 (2002).

Whitesides G.M., et al., "Soft Lithography in Biology and Biochemistry," *Annu. Rev. Biomed. Eng.*, p. 335-373 (2001).

O.D. Velev, et al., "In Situ Assembly of Collordal Particles into Miniaturized Biosensors," *Langmuir*, vol. 15, No. 11, pp. 3693-3698, May 25, 1999.

Ahmadi et al., "Shape-Controlled Synthesis of Colloidal Platinum Nanoparticles", *Science*, Jun. 28, 1996, vol. 272, pp. 1924-1926.

Bahnemann et al., "Mechanisms of Organic Transformations on Semiconductor Particles", *Photochemical Conversion and Storage of Solar Energy*, Proceedings of the Eighth International Conference on Photochemical Conversion and Storage of Solar Energy, IPS-8, held Jul. 15-20, 1990, in Palermo, Italy.

Bassell et al., "Single mRNAs Visualized by Ultrastructural In Situ Hybridization are Principally Localized at Actin Filament Intersections in Fibroblasts", *The Journal of Cell Biology*, Aug. 1994, vol. 126, No. 4, pp. 863-876.

Bottomley et al, "Scanning tunneling microscopy of DNA: The chemical modification of gold surfaces for immobilization of DNA", *J. Vac. Sci. Technol. A*, Jul./Aug. 1992, vol. 10, No. 4, pp. 591-595.

Braun et al., "DNA-templated assembly and electrode attachment of a conducting silver wire", *Nature*, Feb. 19, 1998, vol. 391, pp. 775-778.

Braun-Howland et al., "Development of a Rapid Method for Detecting Bacterial Cells *In Situ* Using 16S rRNA-Targeted Probes", *BioTechniques*, 1992, vol. 13, No. 6, pp. 928-933.

Brus, "Quantum Crystallites and Nonlinear Optics", *Applied Physics A*, 1991, vol. 53 pp. 465-474.

Chrisey et al., "Covalent attachment of synthetic DNA to self-assembled monolayer films", *Nucleic Acids Research*, 1996, vol. 24, No. 15, pp. 3031-3039.

Chrisey et al., "Fabrication of patterned DNA surfaces", *Nucleic Acids Research*, 1996, vol. 24, No. 15, pp. 3040-3047.

Curtis et al., "A Morphology-Selective Copper Organosal", *Angew. Chem. Int. Ed. Engl.*, 1988, vol. 27, No. 11, pp. 1530-1533.

Díaz et al., "Synthesis of Oligodeoxynucleotides Containing 2-Substituted Guanine Derivatives Using 2-Fluoro-2'-Deoxyinosine as Common Nucleoside Precursor", *Nucleosides & Nucleotides*, 1997, vol. 16, Nos. 10 & 11, pp. 2035-2051.

Erlanson et al., "Disulfide Cross-linking as a Mechanistic Probe for the B—Z Transition of DNA", *J. Am. Chem. Soc.*, 1997, vol. 119, pp. 6927-6928.

Goodwin et al., "Incorporation of Alkyithiol Chains at C-5 of Deoxyuridine", *Tetrahedron Letters*, 1993, vol. 34, No. 35, pp. 5549-5552.

Hegner et al., "Immobilizing DNA on gold via thiol modification for atomic force microscopy imaging in buffer solutions", *FEBS*, Dec. 1993, vol. 336, No. 3, pp. 452-456.

Henglein, "Mechanism of Reactions on Colloidal Microelectrodes and Size Quantization Effects", *Topics in Current Chemistry*, 1988, vol. 143, pp. 113-180.

Henglein, "Small-particle Research: Physicochemical Properties of Extremely Small Colloidal Metal and Semiconductor Particles", *Chem. Rev.*, 1989, vol. 89, pp. 1861-1873.

Henglein, "Absorption Spectrum and Some Chemical Reactions of Colloidal Platinum in Aqueous Solution", *J. Phys. Chem.*, 1995, vol. 99, pp. 14129-14136.

Massart, "Preparation of Aqueous Magnetic Liquids in Alkaline and Acidic Media", *IEEE Transactions on Magnetics*, Mar. 1981, vol. MAG-17, No. 2, pp. 1247-1248.

Mansfield et al., "Nucleic acid detection using non-radioactive labeling methods", *Molecular and Cellular Probes*, 1995, vol. 9, pp. 145-156.

Mucic et al., "Synthesis and characterization of DNA with ferrocenyl groups attached to their 5'-termini: electrochemical characterization of a redox-active nucleotide monolayer", *Chemical Communications*, 1996, pp. 555-557.

Nechev et al., "Stereospecific Synthesis of Oligonucleotides Containing Crotonaldehyde Adducts of Deoxyguanosine", *Chem. Res. Toxicol.*, 2001, vol. 14, pp. 1506-1512.

Uchida et al., "GaAs Nanocrystals Prepared in Quinoline", *J. Phys Chem.*, 1991, vol. 95, pp. 5382-5384.

Wang et al., "Nanometer-Sized Semiconductor Clusters: Materials Synthesis, Quantum Size Effects, and Photophysical Properties", *J. Phys. Chem.*, 1991, vol. 95, pp. 525-532.

Weller, "Colloidal Semiconductor Q-Particles: Chemistry in the Transition Region Between Solid State and Molecules", *Angew. Chem. Int. Engl.*, 1993, vol. 32, pp. 41-53.

Zimmermann et al., "DNA stretching on functionalized gold surfaces", *Nucleic Acids Research*, 1994, vol. 22, No. 3, pp. 492-497.

* cited by examiner

ATCGGCTAATCG    [SEQ ID NO:4]
↓ Incorporation of Amino Modifier Phosphoramidite C$_6$-DT
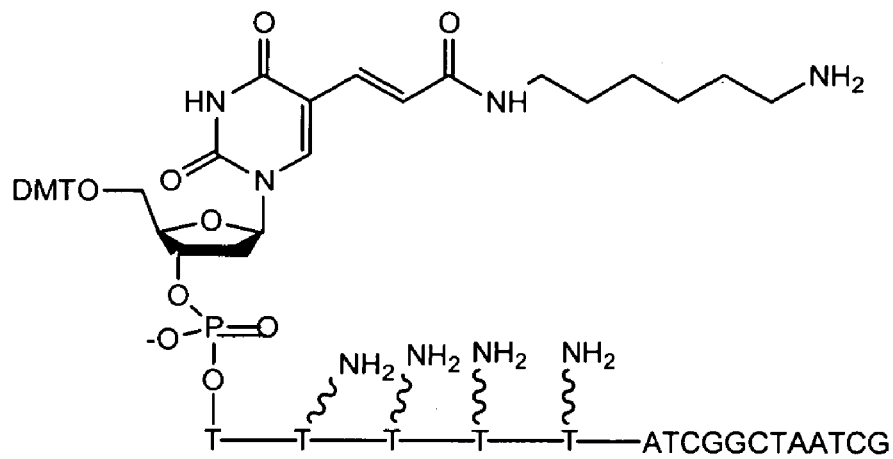
[SEQ ID NO:5]
C$_6$-DT =
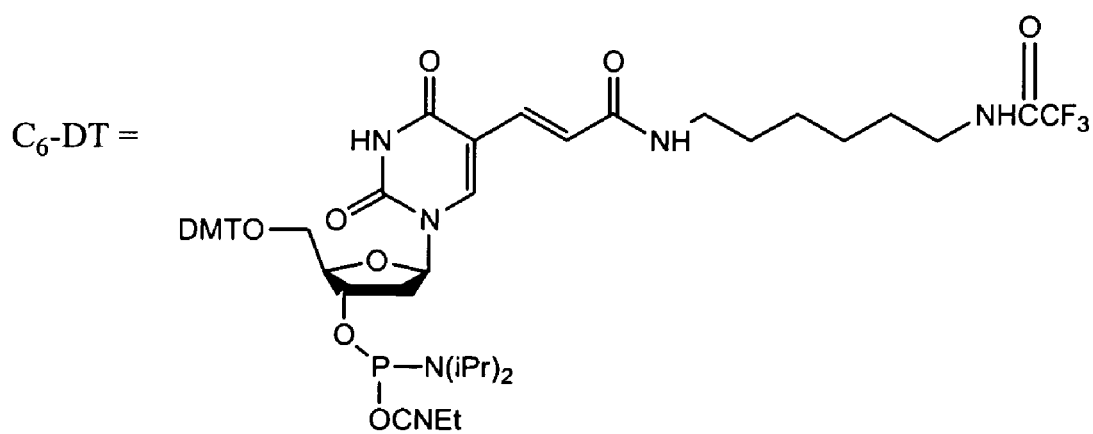
FIG. 3

III

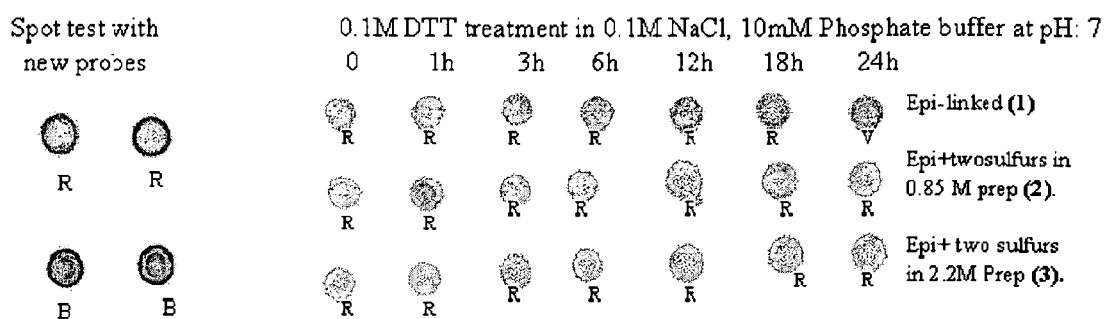
FIG. 10    FIG. 11
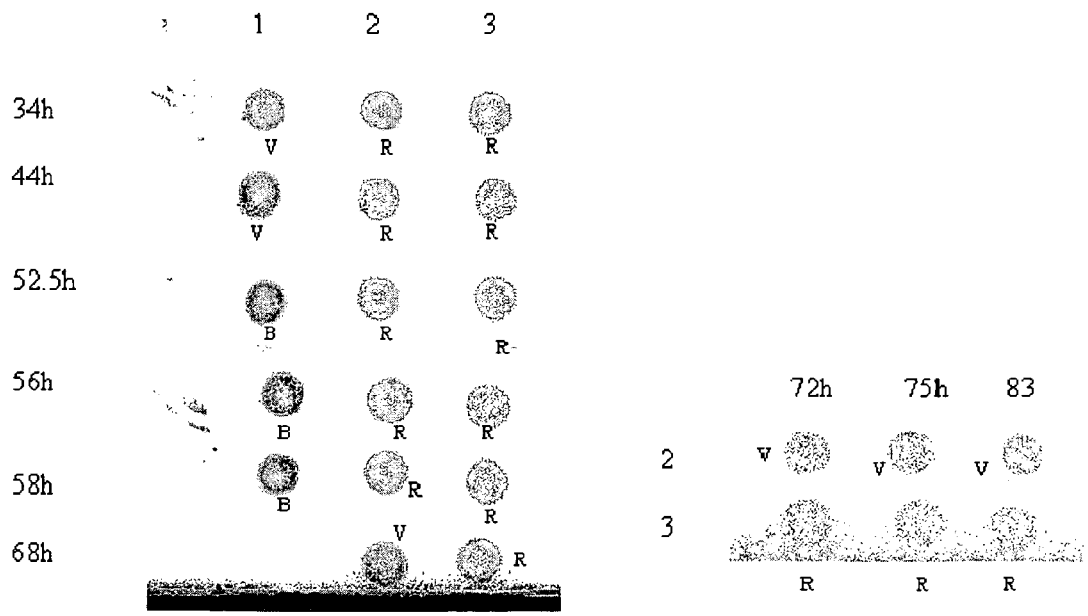
FIG. 12    FIG. 13

```
SEQUENCE LISTING

<160> NUMBER OF SEQ ID NOS: 7

<210> SEQ ID NO 1
<211> LENGTH: 34
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n is epiandrosterone disulfide-SH-SH-

<400> SEQUENCE: 1
naaaaaaaaa aaaaaaaaag cggaagaatg tgtc                             34

<210> SEQ ID NO 2
<211> LENGTH: 34
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n is epiandrosterone disulfide

<400> SEQUENCE: 2
naaaaaaaaa aaaaaaaaaa acctcaaaga aaag                             34
```

```
<210> SEQ ID NO 3
<211> LENGTH: 87
<212> TYPE: DNA
<213> ORGANISM: Artificial sequence
<220> FEATURE:
<223> OTHER INFORMATION: synthetic oligonucleotide

<400> SEQUENCE: 3
ggtgtctgcg ggagccgatt tcatcatcat cacgcagctt ttctttgagg ctgacacatt      60
cttccgcttt gtgaaggcat gcaccga                                          87

<210> SEQ ID NO 4
<211> LENGTH: 12
<212> TYPE: DNA
<213> ORGANISM: Artificial sequence
<220> FEATURE:
<223> OTHER INFORMATION: synthetic oligonucleotide

<400> SEQUENCE: 4
atcggctaat cg                                                          12

<210> SEQ ID NO 5
<211> LENGTH: 17
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(5)
<223> OTHER INFORMATION: n is amino modifier C6-dT

<400> SEQUENCE: 5
nnnnnatcgg ctaatcg                                                     17

<210> SEQ ID NO 6
<211> LENGTH: 17
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(5)
<223> OTHER INFORMATION: thiol modified C6-dT

<400> SEQUENCE: 6
nnnnnatcgg ctaatcg                                                     17

<210> SEQ ID NO 7
<211> LENGTH: 17
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(5)
<223> OTHER INFORMATION: thiol modified C6-dT

<400> SEQUENCE: 7
nnnnnatcgg ctaatcg                                                     17
```

BIOCONJUGATE-NANOPARTICLE PROBES

CROSS REFERENCE

This application claims the benefit of priority from U.S. Provisional application No. 60/348,239, filed Nov. 9, 2001, which is herein incorporated by reference in its entirety.

FIELD OF THE INVENTION

The invention relates to stable bioconjugate-nanoparticle probes which are useful for detecting nucleic acids and other target analytes. The invention also relates to methods for preparing bioconjugate-nanoparticle probes, to methods of detecting target analytes using the probes, and to kits comprising the probes.

BACKGROUND OF THE INVENTION

The development of methods for detecting and sequencing nucleic acids is critical to the diagnosis of genetic, bacterial, and viral diseases. See Mansfield, E. S. et al. Molecular and Cellular Probes, 9, 145–156 (1995). DNA detection methods that employ gold nanoparticle probes, modified with oligonucleotides, to indicate the presence of a particular DNA are described in application number PCT/US00/17507, which is incorporated by reference herein in its entirety. Typically, oligonucleotides having sequences complementary to the nucleic acid to be detected are attached to a nanoparticle. The nanoparticle conjugate hybridized to the nucleic acid results in a detectable change resulting from the hybridization of the oligonucleotide on the nanoparticle to the nucleic acid target in solution.

In order to attach the oligonucleotide to the nanoparticle, the oligonucleotide, the nanoparticle or both, are functionalized. These methods are known in the art and include, for instance, the functionalization of oligonucleotides with alkanethiols at their 3'-termini or 5'-termini. Such functionalized nucleotides readily attach to gold nanoparticles.

A problem associated with nanoparticles derivatized with alkanethiol-oligonucleotides is that the oligonucleotides are easily detached from the nanoparticle surface when the system is heated above a certain temperature. Heating destabilizes and inactivates the nanoparticle-oligonucleotide probes. The oligonucleotides can also be displaced from the nanoparticle surface in the presence of other thiol containing compounds such as DTT.

There exists a need for oligonucleotide-nanoparticle probes, and bioconjugate-nanoparticle probes in general, that exhibit better anchoring of the oligonucleotide to the nanoparticle and are thus more stable and robust. Also needed are methods for preparing such complexes.

SUMMARY OF THE INVENTION

The invention provides a nanoparticle probe comprising a bioconjugate of formula (A) coupled to a nanoparticle:

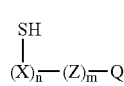
(A)

wherein
n is 2–100;
m is 0–100;
X is a nucleotide, modified oligonucleotide, or a nucleic acid derivative;
Z is a nucleotide, modified oligonucleotide, or polyanion
Q is a recognition group. The bioconjugate is coupled to the nanoparticle through the sulfur groups (—SH).

The invention also provides a nanoparticle probe comprising a bioconjugate of formula (B) coupled to a nanoparticle:

(B)

wherein n, m, X, Z and Q are as defined above for bioconjugate (A), and each L is a linker formed by the coupling of two moieties selected from the group consisting of COOH, $NH_2$, CHO, Cl, Br, I, NCO, NCS, allyl, and $CH_3CO_2^-$, or L is $-C(=NH_2Cl)(CH_2)_3^-$. The bioconjugate is coupled to the nanoparticle through the sulfur groups (—SH).

The invention further provides a nanoparticle probe comprising a bioconjugate of formula (C) coupled to a nanoparticle:

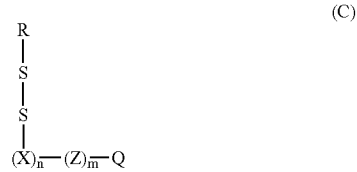
(C)

wherein n, m, X, Z and Q are as defined above for bioconjugate (A), and R is an organic moiety such as an alkyl group such linear or branched $C_1$–$C_8$ alkyl, and wherein the bioconjugate is coupled to the nanoparticle through the disulfide groups (—S—S—).

The invention also provides a nanoparticle probe comprising a bioconjugate of formula (D) coupled to a nanoparticle:

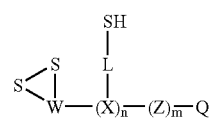
(D)

wherein n, m, X, Z, L and Q are as defined above for bioconjugate (B), and wherein W is an aliphatic or aromatic group. The bioconjugate is coupled to the nanoparticle through the sulfur groups (—SH and S—S).

The invention also provides a nanoparticle probe comprising a bioconjugate of formula (E) coupled to a nanoparticle:

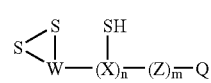
(E)

wherein n, m, X, Z and Q are as defined above for bioconjugate (A), and wherein W is an aliphatic or aromatic group.

The bioconjugate is coupled to the nanoparticle through the sulfur groups (—SH and S—S).

The invention also provides a nanoparticle probe comprising a bioconjugate of formula (F) coupled to a nanoparticle:

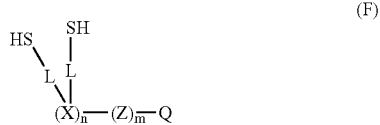

(F)

wherein n, m, X, Z, L and Q are as defined above for bioconjugate (B), and wherein the bioconjugate is coupled to the nanoparticle through the sulfur groups.

The invention also provides a nanoparticle probe comprising a bioconjugate of formula (G) coupled to a nanoparticle:

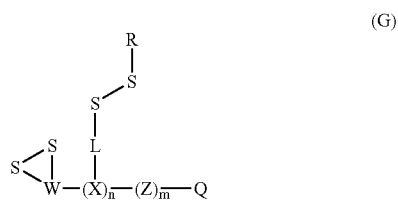

(G)

wherein n, m, X, Z, L, W, R and Q are as defined above. The bioconjugate is coupled to the nanoparticle through the sulfur groups.

The invention also provides methods of preparing bioconjugate-nanoparticle probes, methods of detecting target analytes using the probes and kits comprising the probes of the invention.

As used herein, a "type of oligonucleotides" refers to a plurality of oligonucleotide molecules having the same sequence. A "type of" nanoparticles, particles, latex microspheres, etc. having oligonucleotides attached thereto refers to a plurality of nanoparticles having the same type(s) of oligonucleotides attached to them. "Nanoparticles having bioconjugates attached thereto" are also sometimes referred to as "nanoparticle-bioconjugate probes," "nanoparticle probes," "nano probes," or just "probes."

BRIEF DESCRIPTION OF THE DRAWINGS

FIG. 3 shows a procedure for introducing amine groups into a oligonucleotide.

FIG. 10 depicts a spot test which indicates binding of nanoparticle-probes of the invention to a target.
FIG. 11 depicts spot tests which indicate the relative stability of various nanoparticle-probes in dithiothreitol (DTT) solution.
FIG. 12 depicts spot tests which indicate the relative stability of various nanoparticle-probe in DTT solution.
FIG. 13 depicts spot tests which indicate the relative stability of various nanoparticle-probes in DTT solution.

DETAILED DESCRIPTION OF THE INVENTION

Figure 1:
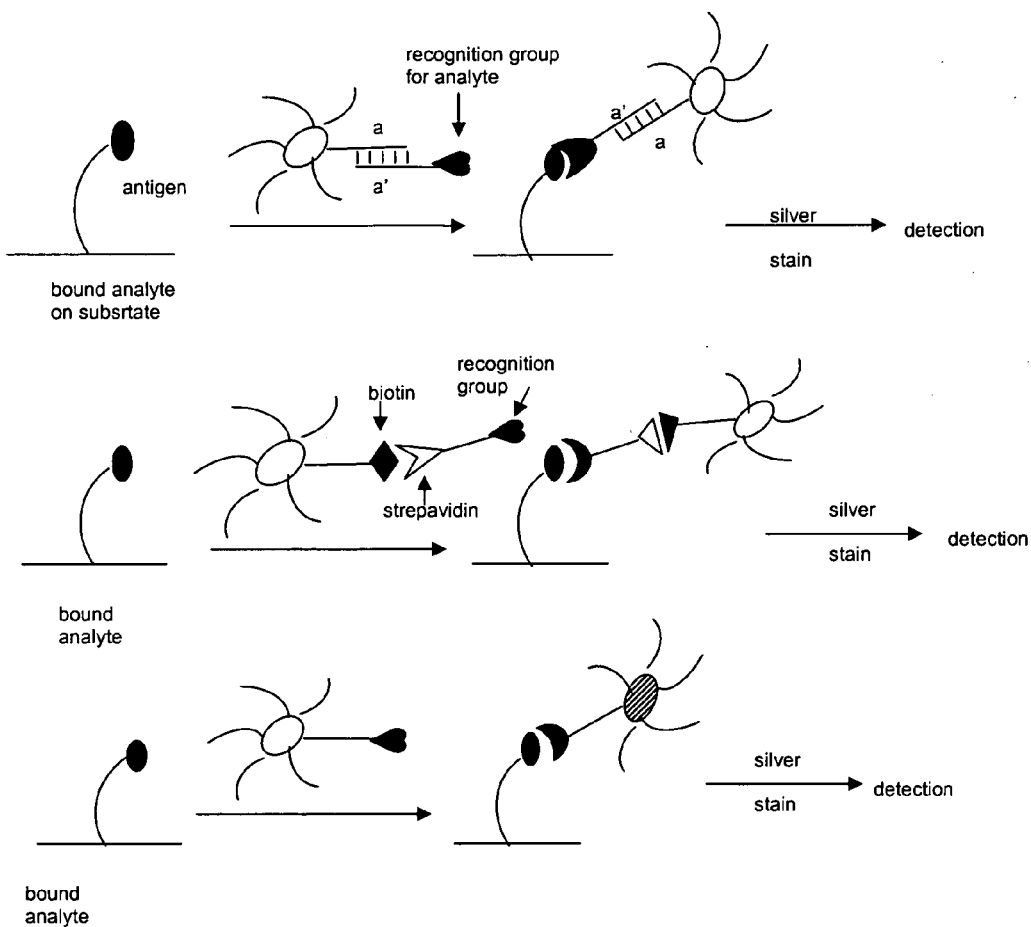
FIG. 1 depicts detection of an analyte using a substrate.

The bio conjugates of formula (A), (B), (C), (D), (E), (F), and (G) provide a solution to the problem of nanoparticle probe instability which results when the probe is heated or subjected to thiol containing compounds. Specifically, the invention permits two or more sulfur groups present on a bioconjugate to bind to the nanoparticle surface, which enhances the stability of the nanoparticle-bioconjugate binding. The resulting bioconjugate nanoparticle probes are stable towards heat and have increased resistance to displacement by thiol containing compounds such as DTT (dithiothreitol).

The bioconjugates that are linked to nanoparticles to form the nanoparticle probes of the invention are of the formulae:

(A)

(B)

(C)

(D)

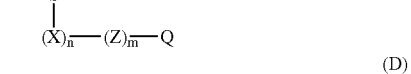

(E)

(F)

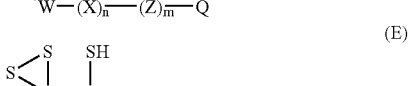

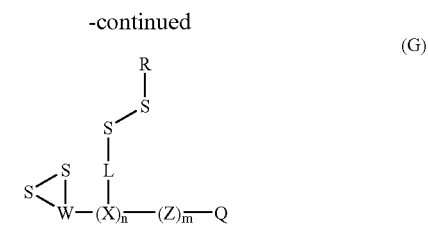

(G)

wherein n, m, X, Z, L, R, W and Q are as defined above.

As indicated above, Q represents a recognition group. By "recognition group" is meant at least one binding moiety with a binding affinity for a target analyte, such as a nucleic acid. Thus, the binding moiety may be, for example, one member of a recognition couple which consists of two or more substances having a binding affinity of one to the other. When a bioconjugate is bound to a nanoparticle, therefore, it provides useful biorecognition properties to the nanoparticle for the analyte. If the target is a nucleic acid, for example, the recognition group can bind to the nucleic acid by hybridization with the nucleic acid. The nucleic acid bound nanoparticle can then be detected.

Examples of recognition groups include, without limitation, a receptor, a nucleotide, a nucleoside, a polynucleotide, an oligonucleotide, double stranded DNA, a protein, an antibody, a peptide, a carbohydrate, a sugar, a hapten, a nucleic acid, an amino acid, a peptide nucleic acid, a linked nucleic acid, a nucleoside triphosphate, a lipid, a lipid bound protein, an aptamer, a virus, a cell fragment, or a whole cell. Examples of recognition group-target analyte couples include: an antigen and an antibody; an antigen and an antibody derivative with a complementary antigen-binding domain; sugar and a lectin; a receptor and a ligand; a nucleotide sequence and a complementary nucleotide sequence; a nucleotide sequence and its binding protein or synthetic binding agent; a biotin and avidin or streptavidin; cellulose or chitin and cellulose binding domain. A preferred recognition group is an oligonucleotide. Also preferred is an antibody.

The recognition group can also be an oligonucleotide having a sequence that is complementary to at least a portion of a second oligonucleotide having a second recognition group, e.g., an oligonucleotide sequence or protein, bound thereto. The second recognition group can then be used for specific binding to a target analyte, e.g., an antigen.

The recognition group can also be a first recognition group, e.g., biotin, that can bind to a second recognition group, e.g., streptavidin, that is a member of the recognition couple. The second recognition group can then be bound directly or indirectly (e.g., via a linker) to a third recognition group, e.g., a receptor, which can bind to a target analyte.

Z, when present, is a nucleotide spacer, a modified oligonucleotide, a polyanion, or other type of spacer which may be utilized in oligonucleotide synthesis such as a polyethylene glycol. It has been found that hybridization efficiency of nanoparticle-bioconjugate probes with nucleic acids can be increased by the use of a spacer portion between the recognition group on the bioconjugate and the nanoparticle. By using a spacer portion, the recognition group is spaced away from the surface of the nanoparticles and is more accessible for hybridization with its target. The length and sequence of the spacer portion providing good spacing of the recognition portion away from the nanoparticles can be determined empirically. It has been found that a spacer portion comprising at least about 10 nucleotides, preferably 10–50 nucleotides, gives good results. The spacer portion may have any sequence which does not interfere with the ability of the recognition group to become bound to a target analyte or a capture moiety on a surface in sandwich hybridization assays. For instance, the spacer portions should not have sequence complementary to each other, to that of the recognition group, or to that of the target analyte. Preferably, the bases of the nucleotides of the spacer portion are all adenines, all thymines, all cytidines, or all guanines, unless this would cause one of the problems just mentioned. More preferably, the bases are all adenines or all thymines. Most preferably the bases are all thymines. Spacer Z and recognition group Q can be attached together by a variety of techniques. For instance, they can be attached directly by a covalent linkage or indirectly by non-covalent linkage.

As a linker, L can be any desired chemical group. For instance, L can be a polymer (e.g., polyethylene glycol, polymethylene, protein, peptide, oligonucleotide, or nucleic acid), —COO—, —CH$_2$(CH$_2$)$_v$COO—, —OCO—, R$^1$N(CH$_2$)$_v$—NR$^1$—, —OC(CH$_2$)$_v$—, —(CH$_2$)$_v$—, —O—(CH$_2$)$_v$—O—, —R$^1$N—(CH$_2$)$_v$—,

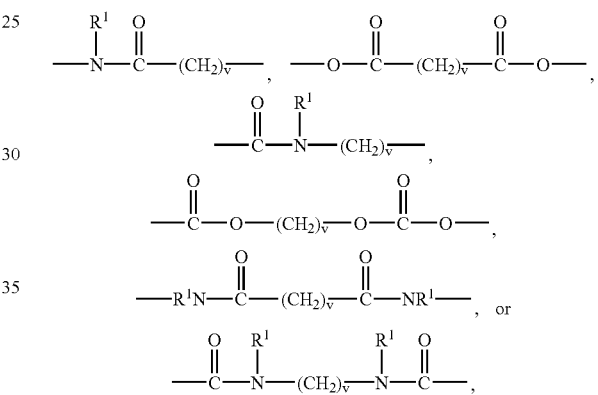

v is 0–30 and R$^1$ is H or is G(CH$_2$)$_v$, wherein G is —CH$_3$, —CHCH$_3$, —COOH, —CO$_2$(CH$_2$)$_v$CH$_3$, —OH, or —CH$_2$OH.

L is also a linker formed by the coupling of two moieties attached to molecules, the moieties selected from the group consisting of COOH, NH$_2$, CHO, Cl, Br, I, NCO, NCS, allyl, and CH$_3$CO$_2^-$, or L is —C(=NH$_2$Cl)(CH$_2$)$_3^-$.

W is an aliphatic or aromatic group on which sulfur moieties can be readily bound. For instance, W can be steroid. Preferably W is an epiandrosterone derivative, as described in example 9.

X represents a nucleotide that has been functionalized with a thiol group (as shown). Preferably, the X groups are all adenines, all thymines, all cytidines, or all guanines, more preferably, all adenines or all thymines, most preferably all thymines. In (X)$_n$, n is 2–100. Preferably, n is 2–50, more preferable 2–20, more preferably 2–10. Functionalization of the X linkage with a thiol group can be carried out by a variety of techniques.

In one embodiment of the invention, either a complex (I) or complex (II) containing at least two reactive groups R$_2$ is synthesized by incorporating nucleotide building blocks containing an R$_2$ group during synthesis of the oligonucleotide. R$_2$ can be COOH, NH$_2$, CHO, F, Cl, Br, I, NCO, NCS, allyl, or CH$_3$CO$_2^-$. If R$_2$ in complex (I) or (II) is an NH$_2$, then a nucleotide derivative containing an NH$_2$ group is prepared for incorporation into the oligonucleotide. Suitable amine modified nucleotide reagents for use in this aspect of the invention include, but are not limited to, $C_6$-dT phosphoramidite (5'-Dimethoxytrityl-5-[N-(trifluoroacetylaminohexyl)-3-acrylimido]-2'-deoxyUridine,3'-[(2-cyanoethyl)-(N,N-diisopropyl)]-phosphoramidite), amino modifier $C_6$-dC (5'-Dimethoxytrityl-N-dimethylformamidine-5-[N-(trifluoroacetylaminohexyl)-3-acrylimido]-2'-deoxy-Cytidine,3'-[(2-cyanoethyl)-(N,N-diisopropyl)]-phosphoramidite), and amino modifier $C_2$-dT (5'-dimethoxytrityl-5-[N-(trifluoroacetylaminoethyl)-3-acrylimido]-2'-deoxy-Uridine,3'-[(2-cyanoethyl)-(N,N-di-isopropyl)]-phosphoramidite). These and other amino modifiers are commercially available, for example from Glen Research, Sterling, Va. A preferred amino modifier reagent is $C_6$-dT.

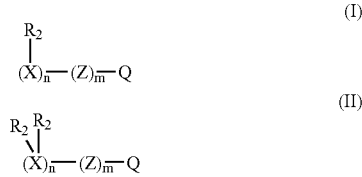

Complex (I) or (II) is reacted with a thiolating reagent that is functionalized with a group capable of reacting with the $R_2$ group on the complex and resulting in formation of a sulfur functionalized bioconjugate. Suitable thiolating reagents generally include thiol compounds possessing one or more functional groups capable of reacting with the $R_2$ group of the complex. Such reagents include, but are not limited to, cystamine, and compounds of the formula $SH(CH_2)_nY$, wherein n is 1–20 and Y is COOH, $NH_2$, CHO, F, Cl, Br, I, NCO, NCS, allyl, or $CH_3CO_2^-$. Another suitable thiolating reagent is 2-iminothiolane hydrochloride (Traut's Reagent), which is preferred when $R_2$ in complex (I) or (II) is an amine. In a preferred aspect of this embodiment, fluorinated nucleotides are incorporated into an oligonucleotide sequence and treated with cystamine to provide disulfide units on the sequence (References (1) L. V. Nechev, I. Kozekov, C. M. Harris, and T. M. Harris, Chem Res Toxicol, 2001, 14, 1506–1512. (2) A. R. Diaz, R. Eritja, and R. G. Garcia, Nucleos Nucleot, 1997, 16, 2035–2051. (3) D. A. Erlanson, J. N. M. Glover, and G. L. Verdine, J. Amer. Chem. Soc., 1997, 119, 6927–6928). This preferred aspect is described in detail in Examples 7–9, below.

An alternative method of thiolating complex (I) or (II) is to use a thiolating reagent that is a combination of reagents. For instance, if $R_2$ in complex (I) or (II) is $NH_2$, then the complex can be treated with an amine reactive bifunctional crosslinker, such as $CHO(CH_2)_nCHO$, and an alkyl or aryl thiol amine, such as $SH(CH_2)_nNH_2$ or $SH(C_6H_4)NH_2$. In both the amine reactive bifunctional crosslinker and the alkyl thiol amine, n is independently 1–30. Preferably, the amine reactive bifunctional crosslinker is glutaraldehyde (i.e., n is 3). Also preferably, the alkyl thiol amine is mercaptoethylamine (i.e., n is 2). Other preferred crosslinkers include 1,4 phenylene diisothiocyanate, 1,6 dihexanoic acid, or 1,6 hexane diisocyanate.

In an alternative and more direct approach for preparing a thiol functionalized bioconjugate, a phosphoramidite containing an alkylthiol or other thiol based group is synthesized and used to prepare a bioconjugate of formula (A). An example of a phosphoramidite containing an alkylthiol group is described in Example 4, below, and is prepared according to the method of Glick et al., *Tetrahedron Letters*, 1993, 34, 5549–5552 which is incorporated herein by reference.

As indicated above, the invention provides bioconjugate nanoparticle probes that are useful for detecting target analytes. To form the probe, bioconjugates (A), (B), (C), (D), (E), (F), or (G) are connected to the surface of a nanoparticle through the sulfur linkages on the bioconjugate. Preferably, the connection is through at least two thiol groups per bioconjugate molecule. Various methods can be used to connect the bioconjugate to the nanoparticle. In fact, any suitable method for attaching a bioconjugate to a nanoparticle may be used. A preferred method for attaching an bioconjugate to a nanoparticle is based on an aging process described in U.S. application Ser. No. 09/344,667, filed Jun. 25, 1999; Ser. No. 09/603,830, filed Jun. 26, 2000; Ser. No. 09/760,500, filed Jan. 12, 2001; Ser. No. 09/820, 279, filed Mar. 28, 2001; Ser. No. 09/927,777, filed Aug. 10, 2001; and in International application Nos. PCT/US97/12783, filed Jul. 21, 1997; PCT/US00/17507, filed Jun. 26, 2000; PCT/US01/01190, filed Jan. 12, 2001; PCT/US01/10071, filed Mar. 28, 2001, the disclosures of which are incorporated by reference in their entirety.

The aging process provides nanoparticle-bioconjugate probes with enhanced stability and selectivity. The method comprises providing bioconjugates having covalently bound thereto thiol functional groups, prepared as described above. The functionalized bioconjugates are contacted with the nanoparticles in water for a time sufficient to allow at least some of the bioconjugates to bind to the nanoparticles by means of the functional groups. Such times can be determined empirically. For instance, it has been found that a time of about 12–24 hours gives good results. Other suitable conditions for binding of the bioconjugates can also be determined empirically. For instance, a concentration of about 10–20 nM nanoparticles and incubation at room temperature gives good results.

Next, at least one salt is added to the water to form a salt solution. The salt can be any suitable water-soluble salt. For instance, the salt may be sodium chloride, lithium chloride, potassium chloride, cesium chloride, ammonium chloride, sodium nitrate, lithium nitrate, cesium nitrate, sodium acetate, lithium acetate, cesium acetate, ammonium acetate, a combination of two or more of these salts, or one of these salts in phosphate buffer. Preferably, the salt is added as a concentrated solution, but it could be added as a solid. The salt can be added to the water all at one time or the salt is added gradually over time. By "gradually over time" is meant that the salt is added in at least two portions at intervals spaced apart by a period of time. Suitable time intervals can be determined empirically.

The ionic strength of the salt solution must be sufficient to overcome at least partially the electrostatic repulsion of the bioconjugates from each other and, either the electrostatic attraction of the negatively-charged bioconjugates for positively-charged nanoparticles, or the electrostatic repulsion of the negatively-charged bioconjugates from negatively-charged nanoparticles. Gradually reducing the electrostatic attraction and repulsion by adding the salt gradually over time has been found to give the highest surface density of bioconjugates on the nanoparticles. Suitable ionic strengths can be determined empirically for each salt or combination of salts. A final concentration of sodium chloride of from about 0.1 M to about 3.0 M in phosphate buffer, preferably with the concentration of sodium chloride being increased gradually over time, has been found to give good results.

After adding the salt, the bioconjugates and nanoparticles are incubated in the salt solution for an additional period of time sufficient to allow sufficient additional bioconjugates to bind to the nanoparticles to produce the stable nanoparticle-bioconjugates probes. An increased surface density of the bioconjugates on the nanoparticles has been found to stabilize the probes. The time of this incubation can be determined empirically. A total incubation time of about 24–48, preferably 40 hours, has been found to give good results (this is the total time of incubation; as noted above; the salt concentration can be increased gradually over this total time). This second period of incubation in the salt solution is referred to herein as the "aging" step. Other suitable conditions for this "aging" step can also be determined empirically. For instance, incubation at room temperature and pH 7.0 gives good results. The solution is then centrifuged and the nanoparticle probes processed as desired. For instance, the solution can be centrifuged at 14,000 rpm in an Eppendorf Centrifuge 5414 for about 15 minutes to give a very pale pink supernatant containing most of the oligonucleotide (as indicated by the absorbance at 260 nm) along with 7–10% of the colloidal gold (as indicated by the absorbance at 520 nm), and a compact, dark, gelatinous residue at the bottom of the tube. The supernatant is removed, and the residue is resuspended in the desired buffer.

The probes produced by use of the "aging" step have been found to be considerably more stable than those produced without the "aging" step. As noted above, this increased stability is due to the increased density of the bioconjugates on the surfaces of the nanoparticles which is achieved by the "aging" step. The surface density achieved by the "aging" step will depend on the size and type of nanoparticles and on the length, sequence and concentration of the oligonucleotides. A surface density adequate to make the nanoparticles stable and the conditions necessary to obtain it for a desired combination of nanoparticles and oligonucleotides can be determined empirically.

Oligonucleotides or other recognition elements containing multiple thiol moieties as described above may bind to a variety of nanoparticles that have an affinity for thiol groups. Nanoparticles useful in the practice of the invention include metal (e.g., gold, silver, platinum, cobalt), semiconductor (e.g., Si, CdSe, CdS, and CdS or CdSe coated with ZnS), core shell particles (e.g., gold coated silver particles), alloy particles (e.g. silver and gold alloy), magnetic (e.g., cobalt), and non metallic (e.g. silicon) colloidal materials. Core shell particles are described in PCT applications PCT/US01/50825, and PCT/US02/16382, as well as copending U.S. application Ser. Nos. 10/153,483 and 10/034,451, each of which is incorporated herein by reference. Other nanoparticles composed of materials that have an affinity for thiol groups may also be used. In addition, nanowires or nanorods having a composition with an affinity for thiol groups also may be used. The size of the nanoparticles is preferably from about 5 nm to about 150 nm (mean diameter), more preferably from about 5 to about 50 nm, most preferably from about 10 to about 30 nm.

Methods of making metal, semiconductor and magnetic nanoparticles are well-known in the art. See, e.g., Schmid, G. (ed.) Clusters and Colloids (V C H, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988). Methods of making $ZnS$, $ZnO$, $TiO_2$, $AgI$, $AgBr$, $HgI_2$, $PbS$, $PbSe$, $ZnTe$, $CdTe$, $In_2S_3$, $In_2Se_3$, $Cd_3P_2$, $Cd_3As_2$, $InAs$, and $GaAs$ nanoparticles are also known in the art. See, e.g., Weller, Angew. Chem. Int. Ed. Engl., 32, 41 (1993); Henglein, Top. Curr. Chem., 143, 113 (1988); Henglein, Chem. Rev., 89, 1861 (1989); Brus, Appl. Phys. A., 53, 465 (1991); Bahncmann, in Photochemical Conversion and Storage of Solar Energy (eds. Pelizetti and Schiavello 1991), page 251; Wang and Herron, J. Phys. Chem., 95, 525 (1991); Olshavsky et al., J. Am. Chem. Soc., 112, 9438 (1990); Ushida et al., J. Phys. Chem., 95, 5382 (1992).

Suitable nanoparticles are also commercially available from, e.g., Ted Pella, Inc. (gold), Amersham Corporation (gold) and Nanoprobes, Inc. (gold). Presently preferred nanoparticles are gold nanoparticles.

The bioconjugate-nanoparticle probes of the invention can be used to detect target analytes, such as nucleic acids. Examples of nucleic acids that can be detected with nanoparticle probes of the invention include genes (e.g., a gene associated with a particular disease), viral RNA and DNA, bacterial DNA, fungal DNA, cDNA, mRNA, RNA and DNA fragments, oligonucleotides, synthetic oligonucleotides, modified oligonucleotides, single-stranded and double-stranded nucleic acids, natural and synthetic nucleic acids, etc. Thus nanoparticle probes prepared according to the invention can be used, for example, for the diagnosis and/or monitoring of viral diseases (e.g., human immunodeficiency virus, hepatitis viruses, herpes viruses, cytomegalovirus, and Epstein-Barr virus), bacterial diseases (e.g., tuberculosis, Lyme disease, *H. pylori, Escherichia coli* infections, Legionella infections, Mycoplasma infections, Salmonella infections), sexually transmitted diseases (e.g., gonorrhea), inherited disorders (e.g., cystic fibrosis, Duchene muscular dystrophy, phenylketonuria, sickle cell anemia), and cancers (e.g., genes associated with the development of cancer); in forensics; in DNA sequencing; for paternity testing; for cell line authentication; for monitoring gene therapy; and for many other purposes.

To perform an assay according to the invention, a sample suspected of containing a target analyte is contacted with bioconjugate nanoparticle probes having attached thereto recognition groups capable of binding to at least a portion of the target analyte. The target to be detected may be isolated by known methods, or may be detected directly in cells, tissue samples, biological fluids (e.g., saliva, urine, blood, serum), solutions containing PCR components, solutions containing large excesses of oligonucleotides or high molecular weight DNA, and other samples, as also known in the art. See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995). Methods of preparing nucleic acids for detection with hybridizing probes are well known in the art. See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995).

If a nucleic acid is present in small amounts, it may be amplified by methods known in the art. See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995). Preferred is polymerase chain reaction (PCR) amplification.

One method according to the invention for detecting nucleic acid comprises contacting a nucleic acid with one or more types of nanoparticle probes of the invention. The nucleic acid to be detected has at least two portions. The lengths of these portions and the distance(s), if any, between them are chosen so that when the bioconjugates on the nanoparticles hybridize to the nucleic acid, a detectable change occurs. These lengths and distances can be determined empirically and will depend on the type of particle used and its size and the type of electrolyte which will be present in solutions used in the assay (as is known in the art, certain electrolytes affect the conformation of nucleic acids).

Also, when a nucleic acid is to be detected in the presence of other nucleic acids, the portions of the nucleic acid to which the bioconjugates on the nanoparticles are to bind must be chosen so that they contain sufficient unique sequence so that detection of the nucleic acid will be specific. Guidelines for doing so are well known in the art.

Although nucleic acids may contain repeating sequences close enough to each other so that only one type of bioconjugate-nanoparticle conjugate need be used, this will be a rare occurrence. In general, the chosen portions of the nucleic acid will have different sequences and will be contacted with nanoparticles carrying two or more different bioconjugates, preferably attached to different nanoparticles. Additional portions of the DNA could be targeted with corresponding nanoparticles. Targeting several portions of a nucleic acid increases the magnitude of the detectable change.

The contacting of the nanoparticle-bioconjugate probes with the nucleic acid takes place under conditions effective for hybridization of the bioconjugates on the nanoparticles with the target sequence(s) of the nucleic acid. These hybridization conditions are well known in the art and can readily be optimized for the particular system employed. See, e.g., Sambrook et al., *Molecular Cloning: A Laboratory Manual* (2nd ed. 1989). Preferably stringent hybridization conditions are employed.

Faster hybridization can be obtained by freezing and thawing a solution containing the nucleic acid to be detected and the nanoparticle-bioconjugate probes. The solution may be frozen in any convenient manner, such as placing it in a dry ice-alcohol bath for a sufficient time for the solution to freeze (generally about 1 minute for 100 microliters of solution). The solution must be thawed at a temperature below the thermal denaturation temperature, which can conveniently be room temperature for most combinations of nanoparticle-bioconjugate probes and nucleic acids. The hybridization is complete, and the detectable change may be observed, after thawing the solution.

The rate of hybridization can also be increased by warming the solution containing the nucleic acid to be detected and the nanoparticle-bioconjugate probes to a temperature below the dissociation temperature (Tm) for the complex formed between the bioconjugates on the nanoparticles and the target nucleic acid. Alternatively, rapid hybridization can be achieved by heating above the dissociation temperature (Tm) and allowing the solution to cool.

The rate of hybridization can also be increased by increasing the salt concentration (e.g., from 0.1 M to 1 M NaCl).

The detectable change that occurs upon hybridization of the bioconjugates on the nanoparticles to the nucleic acid may be an optical change (e.g. color change), the formation of aggregates of the nanoparticles, or the precipitation of the aggregated nanoparticles. The optical changes can be observed with the naked eye or spectroscopically. The formation of aggregates of the nanoparticles can be observed by electron microscopy or by nephelometry. The precipitation of the aggregated nanoparticles can be observed with the naked eye or microscopically. Preferred are color changes observable with the naked eye.

The observation of a color change with the naked eye can be made more readily against a background of a contrasting color. For instance, when gold nanoparticles are used, the observation of a color change is facilitated by spotting a sample of the hybridization solution on a solid white surface (such as silica or alumina TLC plates, filter paper, cellulose nitrate membranes, and nylon membranes, preferably a nylon membrane) and allowing the spot to dry. Initially, the spot retains the color of the hybridization solution (which ranges from pink/red, in the absence of hybridization, to purplish-red/purple, if there has been hybridization). On drying at room temperature or 80° C. (temperature is not critical), a blue spot develops if the nanoparticle-bioconjugate probes had been linked by hybridization with the target nucleic acid prior to spotting. In the absence of hybridization (e.g., because no target nucleic acid is present), the spot is pink. The blue and the pink spots are stable and do not change on subsequent cooling or heating or over time. They provide a convenient permanent record of the test. No other steps (such as a separation of hybridized and unhybridized nanoparticle-bioconjugate probes) are necessary to observe the color change. The color change may be quantitated by recording the plate image with an optical scanning device such as a flatbed scanner or CCD camera, and analyzing the amount and type of color of each individual spot. Alternatively, a color filter (e.g. red filter) may be used to filter out specific colors so that the signal intensity of each spot may be recorded and analyzed.

An alternate method for easily visualizing the assay results is to spot a sample of nanoparticle probes hybridized to a target nucleic acid on a glass fiber filter (e.g., Borosilicate Microfiber Filter, 0.7 micron pore size, grade FG75, for use with gold nanoparticles 13 nm in size), while drawing the liquid through the filter. Subsequent rinsing with water washes the excess, non-hybridized probes through the filter, leaving behind an observable spot comprising the aggregates generated by hybridization of the nanoparticle probes with the target nucleic acid (retained because these aggregates are larger than the pores of the filter). This technique may provide for greater sensitivity, since an excess of nanoparticle probes can be used.

Some embodiments of the method of detecting nucleic acid utilize a substrate. By employing a substrate, the detectable change (the signal) can be amplified and the sensitivity of the assay increased.

Any substrate can be used which allows observation of the detectable change. Suitable substrates include transparent solid surfaces (e.g., glass, quartz, plastics and other polymers), opaque solid surface (e.g., white solid surfaces, such as TLC silica plates, filter paper, glass fiber filters, cellulose nitrate membranes, nylon membranes), and conducting solid surfaces (e.g., indium-tin-oxide (ITO)). The substrate can be any shape or thickness, but generally will be flat and thin. Preferred are transparent substrates such as glass (e.g., glass slides) or plastics (e.g., wells of microtiter plates).

In one embodiment oligonucleotides are attached to the substrate. The oligonucleotides can be attached to the substrates as described in, e.g., Chrisey et al., Nucleic Acids Res., 24, 3031–3039 (1996); Chrisey et al., Nucleic Acids Res., 24, 3040–3047 (1996); Mucic et al., Chem. Commun., 555 (1996); Zimmermann and Cox, Nucleic Acids Res., 22, 492 (1994); Bottomley et al., J. Vac. Sci. Technol. A, 10, 591 (1992); and Hegner et al., FEBS Lett., 336, 452 (1993).

The oligonucleotides attached to the substrate have a sequence complementary to a first portion of the sequence of a nucleic acid to be detected. The nucleic acid is contacted with the substrate under conditions effective to allow hybridization of the oligonucleotides on the substrate with the nucleic acid. In this manner the nucleic acid becomes bound to the substrate. Any unbound nucleic acid is preferably washed from the substrate before adding nanoparticle-bioconjugate probes.

Next, the nucleic acid bound to the substrate is contacted with a first type of nanoparticles having bioconjugates, such as oligonucleotides, attached thereto. The oligonucleotides have a sequence complementary to a second portion of the sequence of the nucleic acid, and the contacting takes place under conditions effective to allow hybridization of the oligonucleotides on the nanoparticles with the nucleic acid. In this manner the first type of nanoparticles become bound to the substrate. After the nanoparticle-oligonucleotide conjugates are bound to the substrate, the substrate is washed to remove any unbound nanoparticle-oligonucleotide conjugates and nucleic acid.

The oligonucleotides on the first type of nanoparticles may all have the same sequence or may have different sequences that hybridize with different portions of the nucleic acid to be detected. When oligonucleotides having different sequences are used, each nanoparticle may have all of the different oligonucleotides attached to it or, preferably, the different oligonucleotides are attached to different nanoparticles. Alternatively, the oligonucleotides on each of the first type of nanoparticles may have a plurality of different sequences, at least one of which must hybridize with a portion of the nucleic acid to be detected.

The first type of nanoparticle-oligonucleotide conjugates bound to the substrate is optionally contacted with a second type of nanoparticles having oligonucleotides attached thereto. These oligonucleotides have a sequence complementary to at least a portion of the sequence(s) of the oligonucleotides attached to the first type of nanoparticles, and the contacting takes place under conditions effective to allow hybridization of the oligonucleotides on the first type of nanoparticles with those on the second type of nanoparticles. After the nanoparticles are bound, the substrate is preferably washed to remove any unbound nanoparticle-oligonucleotide conjugates.

The combination of hybridizations produces a detectable change. The detectable changes are the same as those described above, except that the when second type of conjugates, multiple hybridizations result in an amplification of the detectable change. In particular, since each of the first type of nanoparticles has multiple oligonucleotides (having the same or different sequences) attached to it, each of the first type of nanoparticle-oligonucleotide conjugates can hybridize to a plurality of the second type of nanoparticle-oligonucleotide conjugates. Also, the first type of nanoparticle-oligonucleotide conjugates may be hybridized to more than one portion of the nucleic acid to be detected. The amplification provided by the multiple hybridizations may make the change detectable for the first time or may increase the magnitude of the detectable change. This amplification increases the sensitivity of the assay, allowing for detection of small amounts of nucleic acid.

If desired, additional layers of nanoparticles can be built up by successive additions of the first and second types of nanoparticle-oligonucleotide conjugates. In this way, the number of nanoparticles immobilized per molecule of target nucleic acid can be further increased with a corresponding increase in intensity of the signal.

In one embodiment for detection of non-nucleic acid analytes (see for example U.S. patent application Ser. No. 09/820,279, filed Mar. 28, 2001, and International application PCT/01/10071, filed Mar. 28, 2001, each of which is incorporated herein by reference) the analyte may be bound directly or indirectly, via covalent or non-covalent interactions, to a substrate. The substrates are rthe same type as described above. For indirect binding, the analyte can be bound to the substrate via a linker, e.g., an oligonucleotide or other spacer molecule. Alternatively, the analyte may be modified by binding it to an oligonucleotide having a sequence that is complementary to at least a portion of the sequence of a capture oligonucleotide bound to a substrate. The nanoparticle-probe having a recognition group for the analyte is then contacted with the substrate under conditions effective to allow the specific binding of the nanoparticle-probe to the analyte bound to the substrate and the presence of the analyte can be visually detected either by formation of a spot on the substrate or through the use of staining material such as silver on gold stain. See FIG. 1 for examples of this detection method.

In another method for detecting analytes, the target analyte can be modified by attaching the analyte to the nanoparticle-probe as the recognition portion of the probe. Thereafter, the modified nanoparticle-probe is contacted with a substrate having a second member of the recognition couple bound thereto. The presence of the analyte can be visually detected either by formation of a spot on the substrate or through the use of staining material such as silver on gold stain.

Figure 2:
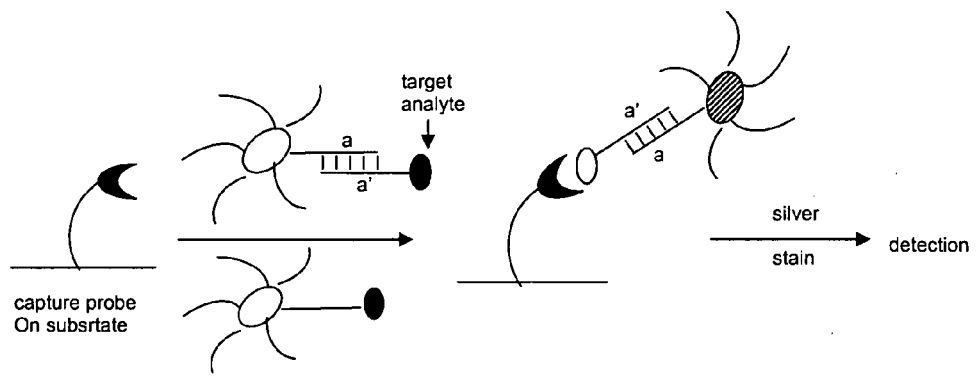
FIG. 2 depicts detection of an analyte using a substrate.

In yet another method for detecting analytes, the target analyte is modified by binding it to an oligonucleotide having a sequence that is complementary to at least a portion of a sequence of an oligonucleotide (recognition group) bound to the nanoparticle-probe. The modified target is then coupled to the nanoparticle-probe by contacting the modified target and the nanoparticle-probe under conditions effective for hybridization between the oligonucleotide bound to the target and the oligonucleotide bound to the nanoparticle-probe. The hybridized complex is then contacted with a substrate having a recognition group for the analyte bound thereto. The presence of the analyte can be visually detected either by formation of a spot on the substrate or through the use of staining material such as silver on gold stain. See FIG. 2 for an example of this method.

When a substrate is employed, a dectectable change can be produced or enhanced by staining. Staining material, e.g., gold, silver, etc., can be used to produce or enhance a detectable change in any assay performed on a substrate, including those described above. For instance, silver staining can be employed with any type of nanoparticles that catalyze the reduction of silver. Preferred are nanoparticles made of noble metals (e.g., gold and silver). See Bassell, et al., *J. Cell Biol.,* 126, 863–876 (1994); Braun-Howland et al., *Biotechniques,* 13, 928–931 (1992). If the nanoparticles being employed for the detection of analyte do not catalyze the reduction of silver, then silver ions can be complexed to the target analyte to catalyze the reduction. See Braun et al., *Nature,* 391, 775 (1998). Also, silver stains are known which can react with the phosphate groups on nucleic acids.

An alternate method for utilizing the polythiol nanoparticle probes is in the application to micro arrays for detecting a variety of biomolecules such as nucleic acids, proteins or carbohydrates. One specific example is the application of polythiol modified oligonucleotide labeled gold nanoparticle probes to the detection of nucleic acids in a sandwich assay format as described in U.S. Pat. No. 6,361,944. In this method, the gold nanoparticle labels are detected via a silver deposition process. Alternatively, a gold nanoparticle development procedure may be used as described in U.S. Pat. No. 6,417,340 and detected optically. It should be noted that the polythiol nanoparticle probes described herein also can be applied as detection probes for use as in situ hybridization labels or expanded to other DNA/RNA detection technologies.

The invention further provides a kit for performing the assays for detecting or quantitating analytes. The kit comprises a container holding nanoparticle probes having recognition groups attached to them. The kit may also contain other reagents and items useful for performing the assays. The reagents may include controls, standards, PCR reagents, hybridization reagents, buffers, etc. Other items which be provided as part of the kit include reaction devices (e.g., test tubes, microtiter plates, solid surfaces (possibly having a capture molecule attached thereto), syringes, pipettes, cuvettes, containers, etc.

The following examples are illustrative of the invention but do not serve to limit its scope.

SYNTHESIS EXAMPLES

Example 1

Introduction of Amino Groups

In this example, amino modifier $C_6$-DT groups are introduced into an oligonucleotide using an amino modifier phosphoramidite (available from Glen Research, Sterling, Va.) (FIG. 3).

Protocol. The amino modifier $C_6$-dT reacts in a manner identical to normal phosphoramidites, i.e., standard automated oligonucleotide synthesis. The trifluoroacetyl (TFA) protecting group on the primary amine is removed during standard ammonium hydroxide deprotection. However, a minor side reaction during ammonia deprotection can lead to irreversibly capping 2–5% of the amine. To prevent this reaction, the synthesis is carried out using acetyl-protected dC and deprotection is carried out in 30% ammonia/40% methylamine 1:1 (AMA) at 65° C. for 15 minutes.

Example 2

Introduction of Thiol Groups

Figure 4:
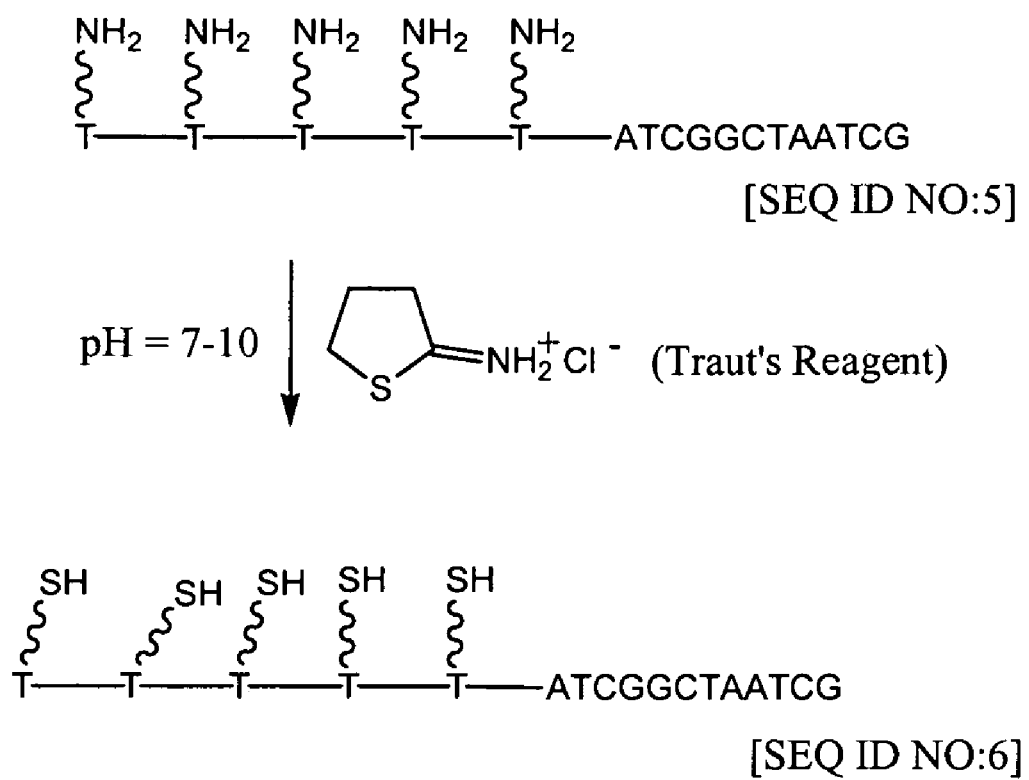
FIG. 4 shows a procedure for introducing thiol groups into a oligonucleotide.

In this example, the amine containing oligonucleotide prepared in Example 1 is reacted with 2-iminothiolane.HCl (Traut's Reagent, available from Pierce Chemical Company, Rockford, Ill.) to introduce thiol groups (FIG. 4).

Protocol. The amine containing oligonucleotide prepared in Example 1 is first purified by reverse phase HPLC and is then dissolved in 50 mM triethanolamine-HCl buffer of pH 8 (or other pH 8 buffer such as 0.16 M Borate of 10 mM phosphate). A 2–10 fold molar excess of 2-iminothiolane-HCl is added. The solution is incubated for 20–60 minutes at 0–25° C. The thiolated amine oligonucleotide is then separated from the amine oligonucleotide using reverse-phase HPLC (0.03 M TEAA buffer (pH 7) with a 1%/min gradient of 95:5 acetonitrile/0.03 M TEAA (pH 7)).

Alternatively, the following protocol can be used. The amine containing oligonucleotide is first purified by reverse-phase HPLC. After purification, the oligonucleotide is re-dissolved in a phosphate or borate buffer (pH 7.2–8.5) containing a 10–100 fold excess of water soluble carbodiimide (WSC, e.g., ethyl dimethylaminopropyl-carbodiimide) and a 10–100 fold excess of 3-mercaptopropionic acid and allowed to stand for 2–4 hours at room temperature. Next, the oligonucleotide is purified through a NAP-10 column to remove excess reagents and eluted in water, followed by reverse-phase HPLC purification.

Example 3

Alternative Protocol for Introduction of Thiol Groups

Figure 5:
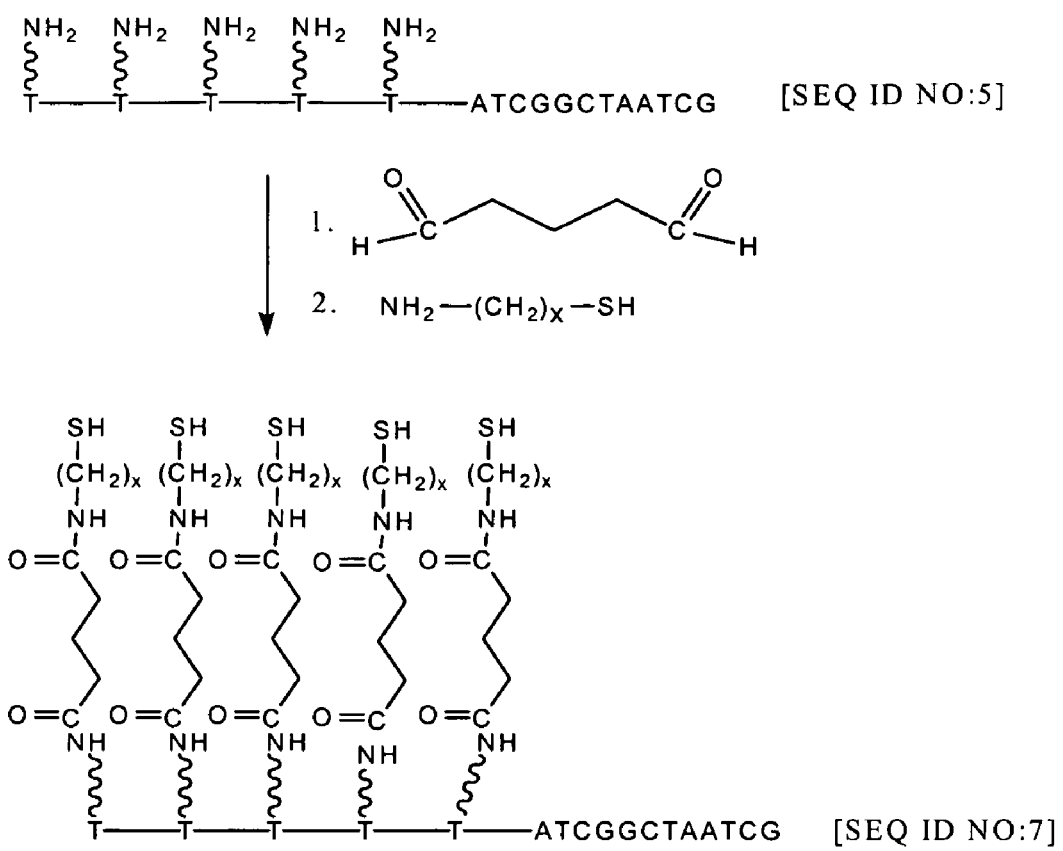
FIG. 5 shows an alternative procedure for introducing thiol groups into a oligonucleotide.

This example presents an alternative method for introducing thiol groups into an oligonucleotide. An amine reactive bifunctional crosslinker, e.g., glutaraldehyde, and a heterobifunctional group such as an alkyl thiol amine are reacted with the amine functionalized oligonucleotide prepared in Example 2, to create thiol groups (FIG. 5).

Protocol. The amine containing oligonucleotide is first purified be reverse-phase HPLC. After purification, the oligonucleotide is redissolved in a phosphate or borate buffer (pH 6–9) containing 10% glutaraldehyde and allowed to stand for 1–2 hours. Next, the oligonucleotide is purified through a NAP-10 column to remove excess glutaraldehyde and eluted in pH 6–9 phosphate or borate buffer. A 10–100 fold excess of mercaptoethylamine is then reacted with the oligonucleotide for 2–4 hours at room temperature, followed by addition of sodium cyanoborohydride to create a 10% solution for 5 min to reduce the Schiff base. The oligonucleotide is subsequently purified by reverse-phase HPLC.

Example 4

Figure 6:
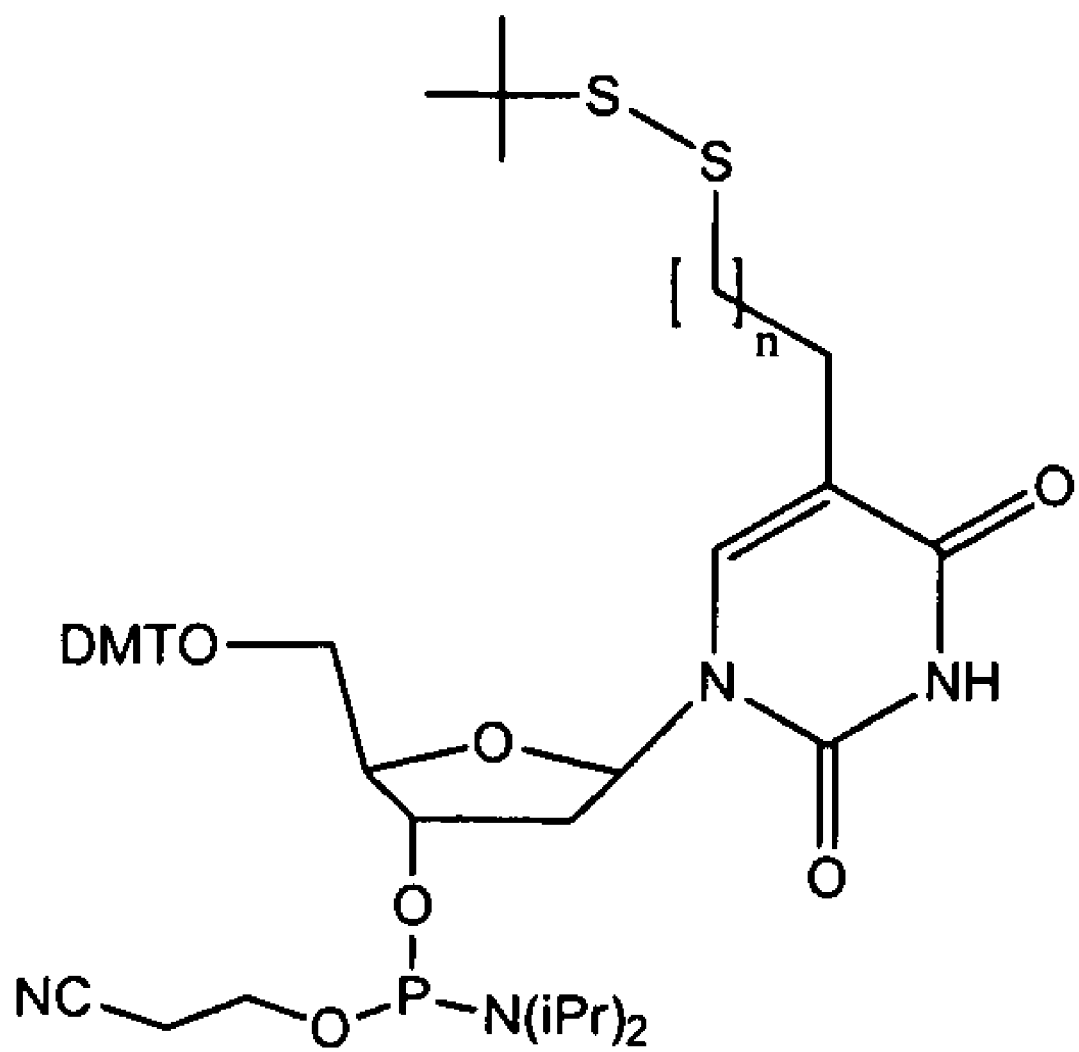
FIG. 6 depicts a phosphoramidite that can be used for introducing thiol groups into an oligonucleotide.

Alternative Protocol for the Introduction of Thiol Groups Using a Thiol Functionalized Phosphoramidite In this example, a phosphoramidite of formula III (FIG. 6) containing an alkyl thiol or other thiol based functionality is synthesized according to the method of Glick et al., *Tetrahedron letters,* 1993, 34, 5549–5552, which is incorporated herein in its entirety. The phosphoramidite is then used to incorporate thiol groups into an oligonucleotide using standard phosphramidite methodology.

Example 5

Alternative Protocol for the Introduction of Thiol Groups

An alternative protocol for the introduction of thiol groups into an oligonucleotide is as follows. Carboxy-dT (available from Glen Research, Sterling, Va.) is introduced into an oligonucleotide in an analogous manner to Example 1. Deprotection is carried out using mild deprotection: 0.4 M methanolic sodium hydroxide (methanol:water 4:1) for 17 hours at room temperature. The support is pipetted off and the solution neutralized with 2 M TEAA. DNA is purified by reverse phase HPLC. The DNA is resuspended in 100 mM MES buffer (pH 6), water soluble coupling reagents are added (ethyl dimethylaminopropyl-carbodiimide (EDC) and -N-hydroxysulfosuccinimide (sulfo NHS)) at a final concentration of 2 mM EDC and 5 mM sulfo-NHS, and the mixture incubated at room temperature for 15 min. Next, a thiol coupling reagent (e.g., $SH(CH_2)_xNH_2$) is added at a 10 fold excess and the mixture incubated at room temperature for 3 hours. The oligonucleotide is purified through a NAP-10 column to remove excess reagents, followed by HPLC purification.

Example 6

Attachment of the Functionalized Nucleotide to a Nanoparticle

In this example the thiol functionalized oligonucleotide prepared by any of the methods disclosed herein is attached to a gold nanoparticle through at least two of the thiol groups.

Protocol. A 4 µM solution of a polythiol modified oligonucleotide is incubated with an approximately 15 nM gold particle dispersion and then the particles isolated by centrifugation.

Example 7

Synthesis of Epiandrosterone Disulfide Derivative (EPI) Modified Oligonucleotides Epiandrosterone can be used as an additional linking element. Its advantages include that it is a readily available, easily derivatized to a ketoalcohol and, as a substituent with a large hydrophobic surface, may help screen the approach of water soluble molecules to the gold surface (Letsinger, et al., J. Am. Chem. Soc. 115, 7535–7536—Bioconjugate Chem. 9, 826–830). Incorporation of the epi disulfide into an oligonucleotide is conducted by phosphoramidite chemistry, as described below.

The epi disulfide derivative has the structure:

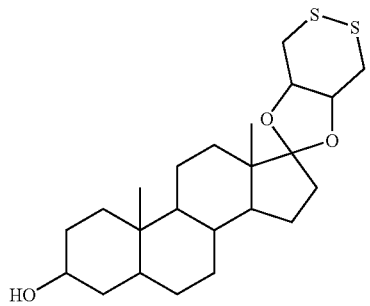

Figure 7:
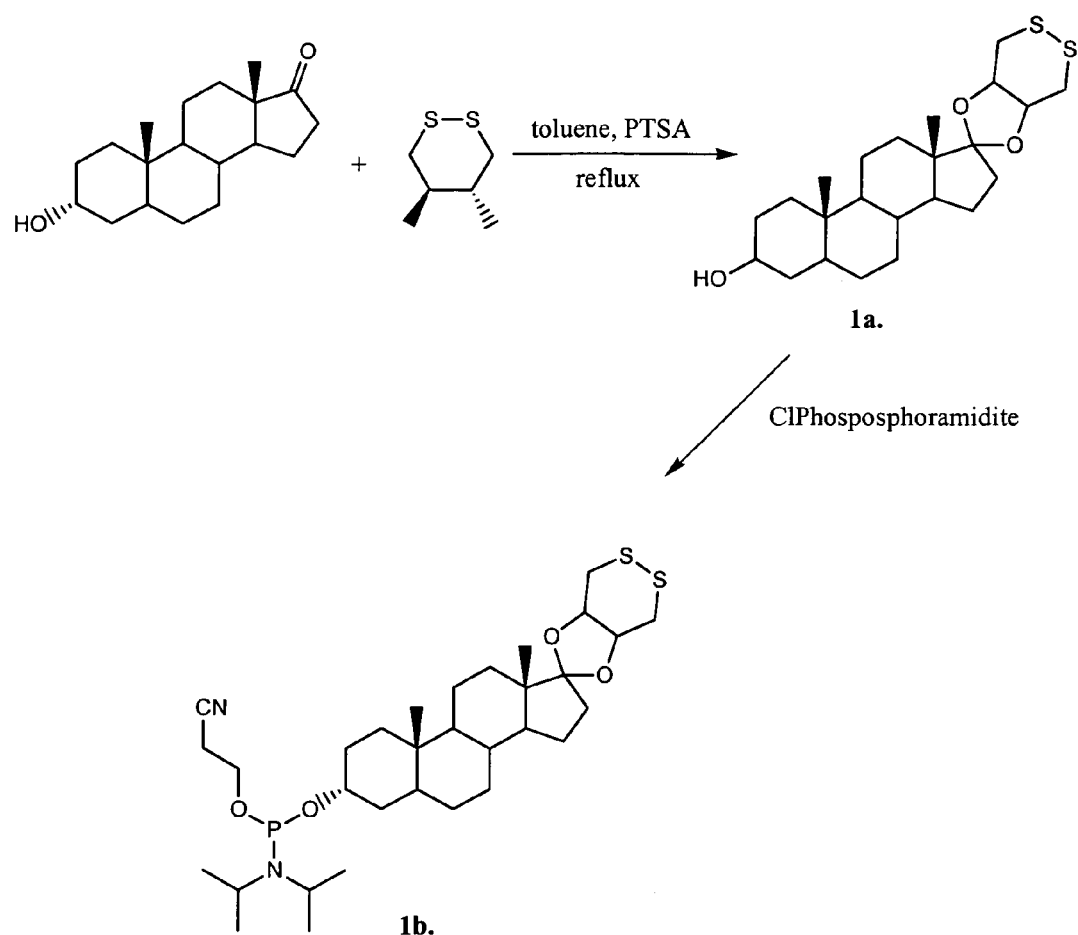
FIG. 7 shows a method for preparing an epiandrosterone disulfide derivatized phosphoramidite.

(a) Synthesis of epi disulfide (FIG. 7). A solution of epiandrosterone (0.5 g), 1,2-dithiane-4,5-diol (0.28 g), and p-toluenesulfonic acid (15 mg) in toluene (30 mL) was refluxed for 7 h under conditions for removal of water (Dean Stark apparatus); then the toluene was removed under reduced pressure and the reside taken up in ethyl acetate. This solution was washed with water, dried over sodium sulfate, and concentrated to a syrupy reside, which on standing overnight in pentane/ether afforded compound epi disulfide 1a as a white solid (400 mg); Rf (TLC, silica plate, ether as eluent) 0.5; for comparison, Rf values for epiandrosterone and 1,2-dithiane-4,5-diol obtained under the same conditions are 0.4, and 0.3, respectively.

Recrystallization from pentane/ether afforded a white powder, mp 110–112° C.; $^1$H NMR, δ 3.6 (1H, C$^3$OH), 3.54–3.39 (2H, m 2OCH of the dithiane ring), 3.2–3.0 (4H, m 2CH$_2$S), 2.1–0.7 (29H, m steroid H); mass spectrum (ES$^+$) calcd for $C_{23}H_{36}O_3S_2$ (M+H) 425.2179, found 425.2151. Anal. ($C_{23}H_{37}O_3S_2$)S: calcd, 15.12; found, 15.26.

(b) Preparation of Steroid-Disulfide Ketal Phosphoramidite Derivative (FIG. 7)

Epi disulfide 1a (100 mg) was dissolved in THF (3 mL) and cooled in a dry ice alcohol bath. N,N-diisopropylethylamine (80 µL) and β-cyanoethyl chlorodiisopropylphosphoramidite (80 µL) were added successively; then the mixture was warmed to room temperature, stirred for 2 h, mixed with ethyl acetate (100 mL), washed with 5% aq. NaHCO$_3$ and with water, dried over sodium sulfate, and concentrated to dryness. The residue was taken up in the minimum amount of dichloromethane, precipitated at −70° C. by addition of hexane, and dried under vacuum; yield 100 mg; $^{31}$P NMR 146.02.

Example 8

Figure 8:
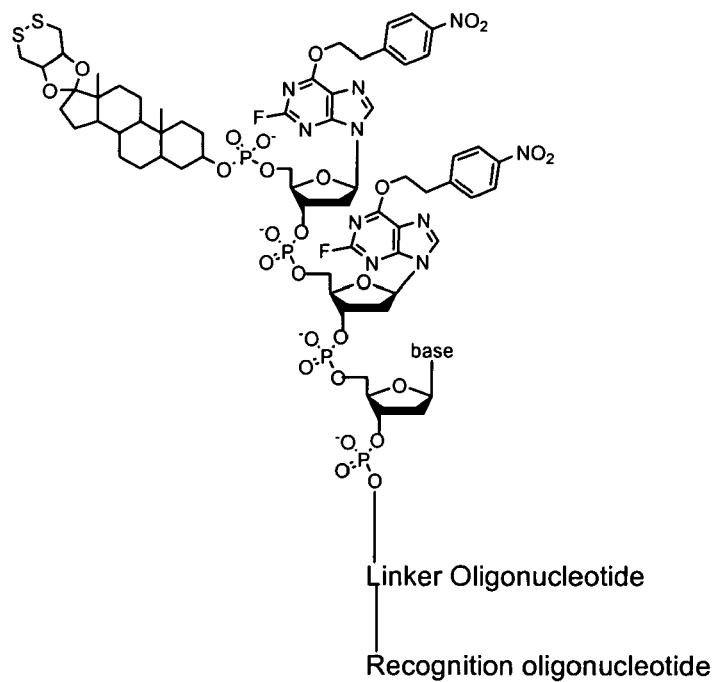
FIG. 8 shows the incorporation of epiandrosterone disulfide into an oligonucleotide.
Figure 9:
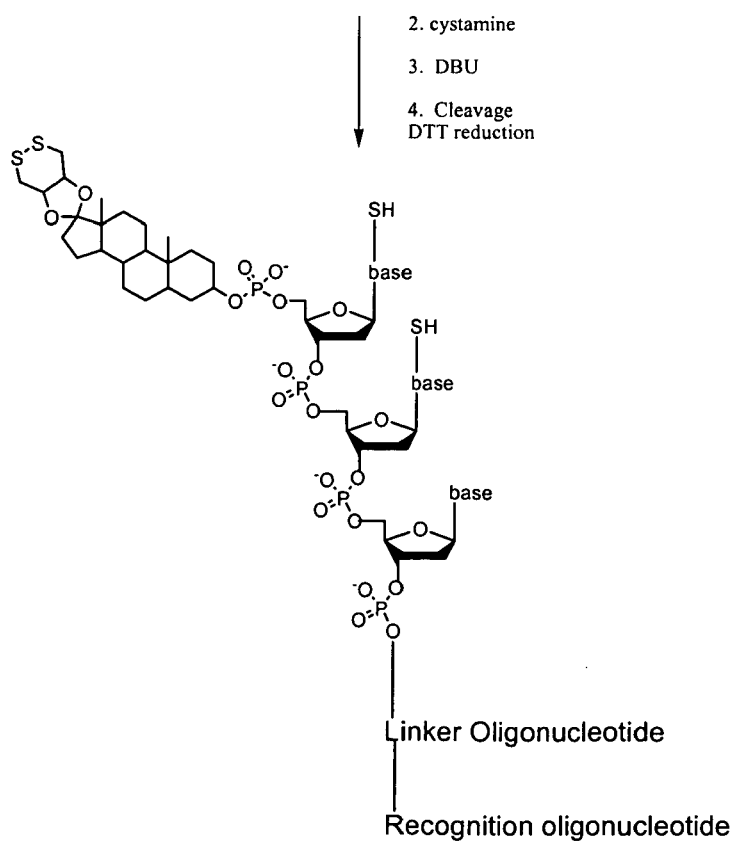
FIG. 9 shows incorporation of additional thiol groups into an oligonucleotide having a epiandrosterone disulfide moiety.

Preparation of 5'-Modified Oligonucleotides
(FIG. 8)

5'-Modified oligonucleotides are constructed on CPG supports using conventional phosphoramidite chemistry, except that compound 1b is employed in the final phosphitilation step. Products are cleaved from the support by treatment with concentrated NH$_4$OH for 16 h at 55° C. The oligonucleotides 1c are purified by reversed phase HPLC on a Dionex DX500 system equipped with a Hewlett Packard ODS Hypersil column (4.6×200 nm, 5 µm particle size) using TEAA buffer (pH 7.0) and a 1%/min gradient of 95% CH$_3$CN/5% 0.03 TEAA at a flow rate of 1 mL/min.

Example 9

Further Thiol Functionalization of 1c by Introduction of Fluorinated Nucleotides and Conversion to Thiol Linked Nucleotides In this example, fluorine modified Inosine nucleotides (2-F-dI; available from Glen Research, Sterling, Va.) are introduced into oligonucleotide 1c and treated with cystamine after completing synthesis. See L. V. Nechev, I. Kozekov, C. M. Harris, and T. M. Harris, Chem Res Toxicol, 2001, 14, 1506–1512; A. R. Diaz, R. Eritja, and R. G. Garcia, Nucleos Nucleot, 1997, 16, 2035–2051; D. A. Erlanson, J. N. M. Glover, and G. L. Verdine, J. Amer. Chem. Soc., 1997, 119, 6927–6928.

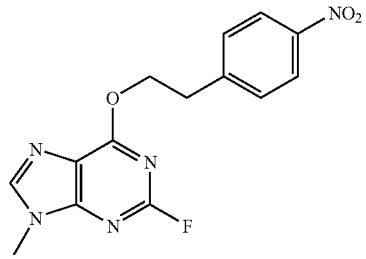

2-F-dI

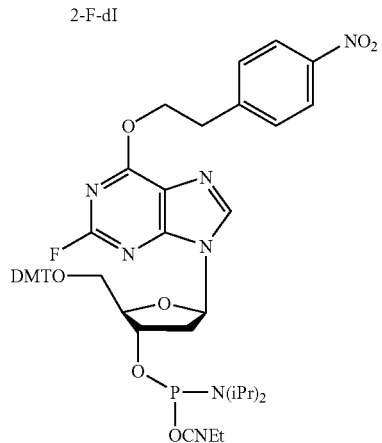

2-F-dI-CE Phosphoramidite

Protocol. 1. Incorporate 2-F-dI at the desired position using standard synthesis conditions with 2-F-dI-CE phosphoramidite (commercially available form Glen Research). 2. Nucleoside Conversion: At the conclusion of oligonucleotide synthesis, rinse the synthesis column with acetonitrile and roughly dry the support with argon. Dissolve desired primary amine in 1–2 mL DMSO (other organic solvent can be substituted depending on solubility of amine) at a concentration of 0.5 M. Treat the support in the column with the amine solution using two 1 mL disposable syringes. Incubate for 18–24 hours at RT to effect conversion. An alternate approach is to transfer the support to a Sarstedt tube, add the amine solution and incubate as above. 3. Preliminary O6 Deprotection: Wash the support 2 times with DMSO then 3 times with acetonitrile and roughly dry the support with argon. Using two disposable syringes as above, treat the support two times with 1 ml each 1M DBU in acetonitrile one hour each time. Rinse the support with 1 ml each of methanol X 2, and acetonitrile X 3. Roughly dry the support with argon and deprotect the oligo 1d from the support using ammonium hydroxide as normal.

STABILITY EXAMPLES

Stability of the nanoparticle probes of the invention was evaluated by spotting the subject mixtures on a solid white surface (such as a C-18 silica TLC plate or a reversed phase (RP) HPLC plate) and observing the color of the spot after drying. Red indicates starting nanoparticle with DNA strands on dispersed in solution, and violet indicates particle aggregation due to partial displacement of oligonucleotides on the gold nanoparticle, and blue indicates even greater particle aggregation due to more extensive displacement of oligonucleotides.

Example 10

EPI+2S Probes

Oligonucleotides having the sequence 5'-Epi-SH-SH-al 8-gcg gaa gaa tgt gtc-3' [SEQ ID NO:1] were prepared as described in Examples 7–9. These oligonucleotides have an analogous structure to oligonucleotides 1d in FIG. 7, i.e., they possess an epi disulfide moiety and two further thiol groups on the backbone. The oligonucleotides are loaded onto gold nanoparticles as described below. The probes are representative of probes of the invention and are denoted "EPI+2S probes."

EPI+2S probes are prepared (loaded) in two different salt solutions; the same oligonucleotide is loaded in either 0.85 M sodium chloride or in 2.2 M sodium chloride. The EPI-2S probes' length is 35 mer total and contains no fillers.

Attachment of Oligonucleotides to Gold Nanoparticles

A colloidal solution of citrate stabilized gold nanoparticles (about 10 nM), prepared by the citrate reduction method (Grabar et. al, Anal. Chem. 1995, 67, 735.), was mixed with sulfur modified-$a_{20}$-probe oligonucleotide (4 µM), and allowed to stand for 24 hours at room temperature in 1 ml Eppendorf capped vials. Then, Step 1: 100 µL of a 0.1 M sodium hydrogen phosphate buffer, pH 7.0, and 100 µL of 1.0 M NaCl were premixed and added to the solution and allowed to stand for an additional 12 hours. Step2: Then the salt concentration was increased to 0.3M NaCl and kept further 12 h at room temperature. Step 3: At this point the salt concentration was increased to 0.85 and kept another 16 h at room temperature. Total salt aging process took 40 h. In the case of the 2.2 M salt concentration, work up at the stage of step 3 salt was increased gradually to 2.2 M NaCl and kept at room temperature.

The solution was next centrifuged at 14,000 rpm in an Eppendorf Centrifuge 5414 for about 15 minutes to give a very pale pink supernatant containing most of the oligonucleotide (as indicated by the absorbance at 260 nm) along with 7–10% of the colloidal gold (as indicated by the absorbance at 520 nm), and a compact, dark, gelatinous residue at the bottom of the tube. The supernatant was removed, and the residue was re suspended in the desired buffer.

Example 11

EPI Probes

Oligonucleotides having an analogous structure to oligonucleotide 1c, i.e., possessing an epi disulfide linkage but no other sulfur groups, were prepared as described in Examples 7–8. The probe length is 18mer+A20 linker and total 38mer. The probe sequence is 5'-Epi-a20-cct caa aga aaa g-3' [SEQ ID NO:2] and A20-Epi filler. The probe is loaded in 0.85 M NaCl solution. These probes are representative of prior art probes in that they do not contain additional thiol functionalization of the oligonucleotide backbone. The probes are denoted "EPI probes."

Attachment of Oligonucleotides to Gold Nanoparticles:

A colloidal solution of citrate stabilized gold nanoparticles (about 10 nM), prepared by the citrate reduction method (Grabar et. al, Anal. Chem. 1995, 67, 735.) was mixed with sulfur modified-$a_{20}$-probe oligonucleotide and corresponding sulfur modified-$da_{20}$ filler oligonucleotide (each to a concentration of 1.7 µM), prepared as described in part B, and allowed to stand for 24 hours at room temperature in 1 ml Eppendorf capped vials. Then, Step 1: 100 µL of a 0.1 M sodium hydrogen phosphate buffer, pH 7.0, and 100 µL of 1.0 M NaCl were premixed and added to the solution and allowed to stand for an additional 12 hours. Step2: Then salt concentration was increased to 0.3M NaCl and kept further 12 h at room temperature. Step 3: At this point salt concentration was increased to 0.85 and kept another 16 h at room temperature. Total salt aging process took 40 h.

The solution was next centrifuged at 14,000 rpm in an Eppendorf Centrifuge 5414 for about 15 minutes to give a very pale pink supernatant containing most of the oligonucleotide (as indicated by the absorbance at 260 nm) along with 7–10% of the colloidal gold (as indicated by the absorbance at 520 nm), and a compact, dark, gelatinous residue at the bottom of the tube. The supernatant was removed, and the residue was resuspended in the desired buffer.

Example 12

Binding of EPI+2S to a Target

This example verified that EPI+2S probes, like EPI probes, bind to a target.

To 100 µl of a colloid mixture (50 µl of EPI+2S probes and 50 µl of EPI probes), 1 µl of a 10 µM solution of the target (MTHFR 87 mer synthetic target) was added and the sample frozen at −70° C. for 1 minute and then thawed at room temperature. After the sample was brought to room temperature, 3 µl aliquots were spotted on a RP HPLC plate and solvents evaporated. Simultaneously, control solution prepared in a similar manner but without target was spotted on the HPLC plate. After evaporation of the solvents, the target containing spot turned completely blue, indicating hybridizing to the target. The control spot turned red, indicating absence of hybridization. See FIG. 10. FIG. 10 shows binding of the oligonucleotide to a target. In the figure, R indicates red, B indicates blue and P indicates purple. The target in this example has the sequence 87mer target: 5'-ggt gtc tgc ggg agc cga ttt cat cat cat cac gca gct ttt ctt tga ggc tga cac att ctt ccg ctt tgt gaa ggc atg cac cga-3' [SEQ ID NO:3].

Example 13

Stability in the Presence of DTT

This example shows the increased stability of EPI+2S probes in DTT solution, in comparison to EPI probes. The example also shows that EPI+2S probes prepared in 2.2 M NaCl solution ("2.2 M EPI+2S probes") are more stable than EPI+2S probes prepared in 0.85 M NaCl solution ("0.85 M EPI+2S probes").

To 50 µl of the probe colloid in 0.1 M NaCl and 10 mM Phosphate buffer at pH 7, 5 µl of 0.1M DTT solution was added and the mixture spotted on a C-18 RP silica plate. The EPI probe spot turned blue in 44 h. The 0.85 M loading EPI+2S probe spot turned blue within 72 h, indicating greater stability than the EPI probes. As expected, the 2.2 M loading EPI+2S probe spot did not turn blue even after 83 h in 0.1M NaCl conditions, indicating even greater stability. See FIGS. 11–13. FIGS. 11–13 show displacement of the oligonucleotide from the nanoparticle (indicated by a blue spot).

Example 14

Stability in the Presence of DTT at Elevated Temperature

This example reveals the increased stability of EPI+2S probes in the presence of DTT at elevated temperature, compared with EPI probes.

Figure 14:
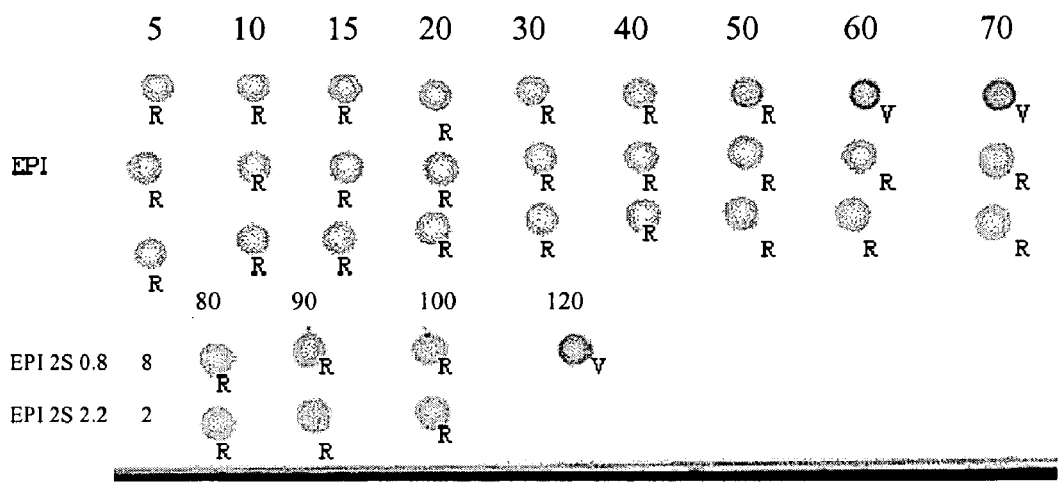
FIG. 14 depicts spot tests which indicate the relative stability of various nanoparticle-probes in DTT solution at elevated temperature.

To 50 µl of the colloid, 5 µl of 0.1M DTT solution was added and incubated at 60° C. and spotted on a C-18 RP silica plate. The EPI probe turned blue in 70 min, whereas the 0.85 M EPI-2S probe started turning blue at 120 min. See FIG. 14. FIG. 14 shows displacement of the oligonucleotide from the nanoparticle (indicated by a blue spot).

Example 15

Stability in the Presence of DTT and MgCl$_2$ at Elevated Temperature

This example shows the increased stability of EPI+2S probes in the presence of DTT and MgCl$_2$ at elevated temperature, compared with EPI probes.

Figure 15:
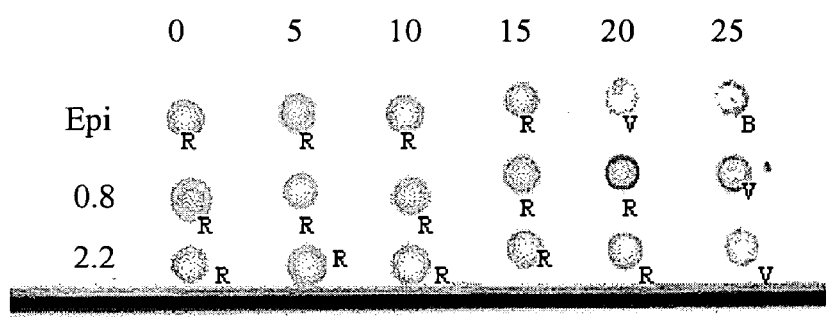
FIG. 15 depicts spot tests which indicate the relative stability of various nanoparticle-probes in DTT solution, at elevated temperature and in the presence of magnesium chloride solution.

To 50 µl of the colloid, 5 µl of 0.1 M DTT solution and 10 mM MgCl$_2$ [final concentration] were added and the samples incubated at 60° C. The samples were spotted on a C-18 RP silica plate. The EPI probe spot turned blue in 25 min while the 0.85 M EPI-2S probe spot started turning blue at 25 min. The 2.2 M EPI-2S probe spot also started turning blue at 25 min. See FIG. 15. FIG. 15 shows displacement of the oligonucleotide from the nanoparticle (indicated by a blue spot).

The invention claimed is:

1. A method for preparing a nanoparticle-probe, the nanoparticle-probe comprising a bioconjugate coupled to a nanoparticle, the method comprising:

(i) reacting a thiol modifier reagent having a structure of formula:

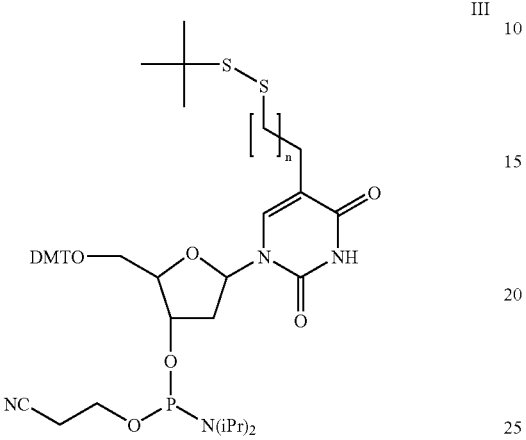

III wherein n is 1–10, with a structure of formula:

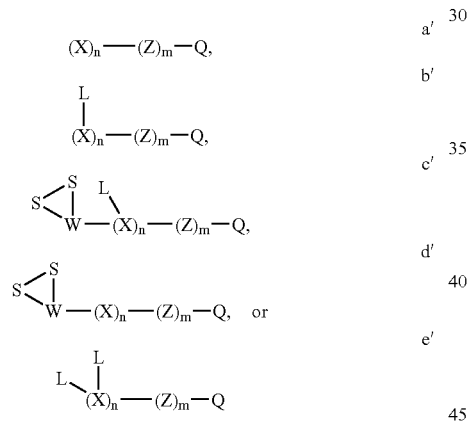

a'
b'
c'
d'
e' to produce a disulfide having the formula

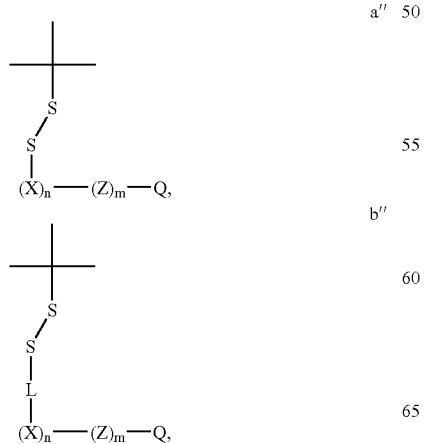

a"
b"

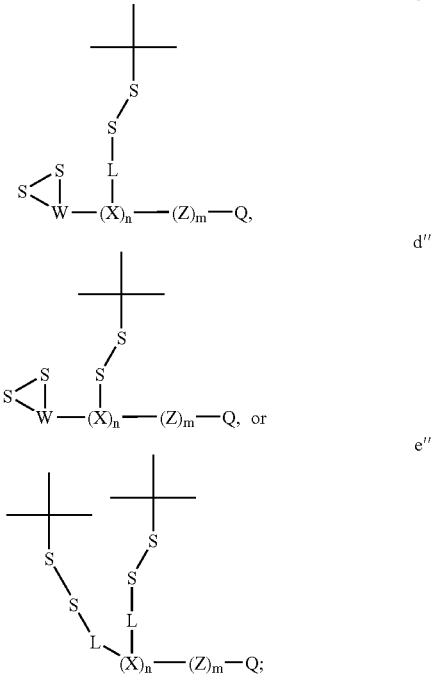

c"
d"
e"

(ii) reducing the disulfides a", b", c", d" or e" of (i) to produce a bioconjugate having formula:

 (A)

 (B)

 (D)

 (E)

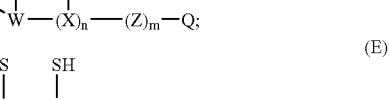 (F)

and (iii) contacting one or more of the bioconjugates of (ii) with a nanoparticle to form the nanoparticle-probe, wherein the bioconjugate is coupled to the nanoparticle through the sulfur groups: wherein n is 2–100;
m is 0–100;
X is a nucleotide or modified nucleotide;
Z is a nucleotide, modified oligonucleotide, or polyanion;
Q is a recognition group;

R is linear or branched $C_1$–$C_8$ alkyl;

W is a steroid; and each L is a linker formed by the coupling of two moieties selected from the group consisting of COOH, $NH_2$, CHO, F, Cl, Br, I, NCO, NCS, allyl, vinyl, and $CH_3CO_2^-$, or L is —C(=$NH_2$Cl)($CH_2$)$_3$—.

2. The method of claim 1, wherein the bioconjugate is bioconjugate (B) and step (ii) comprises:

contacting the bioconjugate (B) with the nanoparticle in water;

adding a salt to the water to form a salt solution;

incubating the bioconjugate and nanoparticle in the salt solution to form a bioconjugate-nanoparticle probe; and isolating the bioconjugate-nanoparticle probe from the salt solution.

3. The method of claim 2, wherein all of the salt is added to the water in a single addition.

4. The method of claim 2, wherein the salt is added gradually over time.

5. The method of claim 2, wherein the salt is selected from the group consisting of sodium chloride, magnesium chloride, potassium chloride, ammonium chloride, sodium acetate, ammonium acetate, a combination of two or more of these salts, one of these salts in a phosphate buffer, and a combination of two or more these salts in a phosphate buffer.

6. The method of claim 5, wherein the salt is sodium chloride in a phosphate buffer.

7. The method of claim 2, wherein the nanoparticle is selected from the group consisting of a metal, a semiconductor, a magnetic material, a colloidal material, ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, GaAs, GaP, $BaTiO_3$, Co, $Fe_2O_3$, core shell particles and alloyed particles.

8. The method of claim 7, wherein the nanoparticle is gold.

9. The method of claim 1, wherein the bioconjugate is bioconjugate (A).

10. The method of claim 1, wherein Q in the bioconjugate comprises an organic molecule, an organic or inorganic polymer, a receptor, a nucleotide, a nucleoside, a polynucleotide, an oligonucleotide, a protein, an antibody, a peptide, a carbohydrate, a sugar, a hapten, a nucleic acid, an amino acid, a peptide nucleic acid, a linked nucleic acid, a nucleoside triphosphate, a lipid, a lipid bound protein, an aptamer, a virus, a cell fragment, or a whole cell.

11. The method of claim 1, wherein the recognition group comprises a first and a second recognition group, wherein the first recognition group is bound to the second recognition group and wherein the second recognition group is a member of a recognition couple that specifically binds to a target analyte.

12. The method of claim 11, wherein the first and second recognition groups comprise a specific binding pair.

13. The method of claim 12, wherein the binding pair is an antibody-antigen or a receptor-ligand.

14. The method of claim 11, wherein the first and second recognition groups are oligonucleotides having at least a portion of its sequence complementary to each other.

15. The method of claim 1, wherein X and Z are independently adenine, guanine, cystosine, thymine, uracil, a nucleotide derivative, a modified nucleotide, or other molecules that may be incorporated into the oligonucleotide synthesis process.

16. The method of claim 15, wherein X is thymine.

17. The method of claim 1, wherein L is —NH—C(=O)—.

18. The method of claim 1, wherein n from bioconjugate D is 2.

19. The method of claim 10, wherein Q is an oligonucleotide.

20. The method of claim 10, wherein Q is a cDNA.

21. The method of claim 10, wherein Q is a polynucleotide.

22. The method of claim 1, wherein the nanoparticle is selected from nanoparticles that have an affinity for thiol groups.

23. The method of claim 22, wherein the nanoparticle is selected from the group consisting of a metal, a semiconductor, a magnetic material, including Au, Ag, Pt, Co, CdSe, CdS, or Si.

24. The method of claim 23, wherein the nanoparticle is gold.

25. The method of claim 1, wherein prior to step (iii), further comprising reacting bioconjugates A or D of step (ii) with

[structure: 2-pyridyl-S-S-R]

to produce a bioconjugate having the formula (C)

[structure showing R-S-S-(X)$_n$-(Z)$_m$-Q]

or (G)

[structure showing R-S-S with W-(X)$_n$-(Z)$_m$-Q and L branch]

* * * * *